(12) United States Patent
Weinberg et al.

(10) Patent No.: US 12,347,531 B2
(45) Date of Patent: Jul. 1, 2025

(54) METHOD AND APPARATUS OF CHEMISTRY EDUCATION

(71) Applicant: TOPHATMONOCLE (US) CORP., Toronto (CA)

(72) Inventors: Justin Weinberg, New York, NY (US); Igor Belyayev, New York, NY (US); Amanda Kutney, Atlanta, GA (US); Sazzad Hossain, Jamaica, NY (US)

(73) Assignee: TOPHATMONOCLE (US) CORP., Toronto (CA)

( * ) Notice: Subject to any disclaimer, the term of this patent is extended or adjusted under 35 U.S.C. 154(b) by 1147 days.

(21) Appl. No.: 17/200,281

(22) Filed: Mar. 12, 2021

(65) Prior Publication Data

US 2022/0293012 A1    Sep. 15, 2022

(51) Int. Cl.
| | | |
|---|---|---|
| *G01N 33/48* | (2006.01) | |
| *G06F 3/0484* | (2022.01) | |
| *G09B 5/02* | (2006.01) | |
| *G09B 23/24* | (2006.01) | |
| *G16C 20/80* | (2019.01) | |

(52) U.S. Cl.
CPC .......... *G16C 20/80* (2019.02); *G06F 3/0484* (2013.01); *G09B 5/02* (2013.01); *G09B 23/24* (2013.01)

(58) Field of Classification Search
None
See application file for complete search history.

(56) References Cited

U.S. PATENT DOCUMENTS

| | | |
|---|---|---|
| 9,430,127 B2 | 8/2016 | Smith et al. |
| 9,535,583 B2 | 1/2017 | Smellie et al. |
| 10,424,399 B2 | 9/2019 | Clark et al. |
| 10,453,560 B2 | 10/2019 | Morieux et al. |
| 10,790,046 B2 | 9/2020 | Smith et al. |
| 2014/0173475 A1* | 6/2014 | Smellie .................. G16C 20/80 715/765 |
| 2014/0337725 A1* | 11/2014 | Smith ................... G06F 3/0486 715/702 |
| 2019/0236244 A1* | 8/2019 | Morieux ............... G06F 3/0484 |
| 2020/0035334 A1* | 1/2020 | Morieux ............... G16C 20/90 |

* cited by examiner

*Primary Examiner* — Anna Skibinsky
(74) *Attorney, Agent, or Firm* — Fishman Stewart PLLC

(57) ABSTRACT

A non-transitory computer-readable medium storing instructions executable by a hardware processor to create a plurality of adaptive grids, present an adaptive hexagon grid in a drawing window on a display, prompt a user to create a first chemical structure on the adaptive hexagon grid, present a first plurality of atomic bond representations on the display, receive a first location selection chosen by the user from the adaptive hexagon grid, present a first plurality of atomic bond representations on the display, receive a first atomic bond selection chosen by the user from the first plurality of atomic bond representations, and present the first atomic bond selection at the first location selection on one of the plurality the adaptive grids. The first plurality of atomic bond representations include at least a single covalent bond representation and a double covalent bond representation.

20 Claims, 15 Drawing Sheets

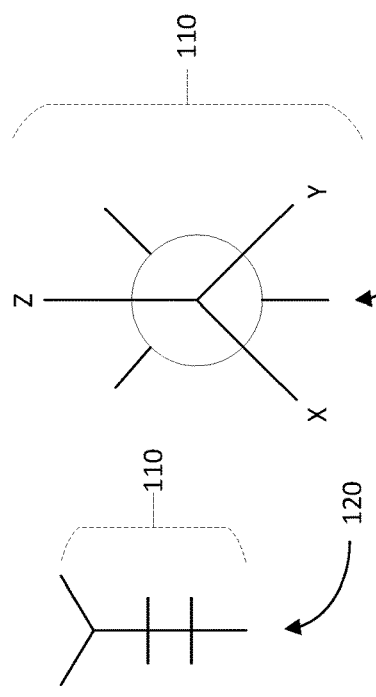
FIG. 1B
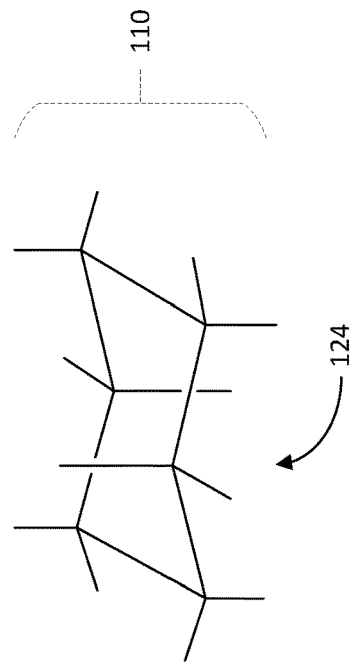
FIG. 1C
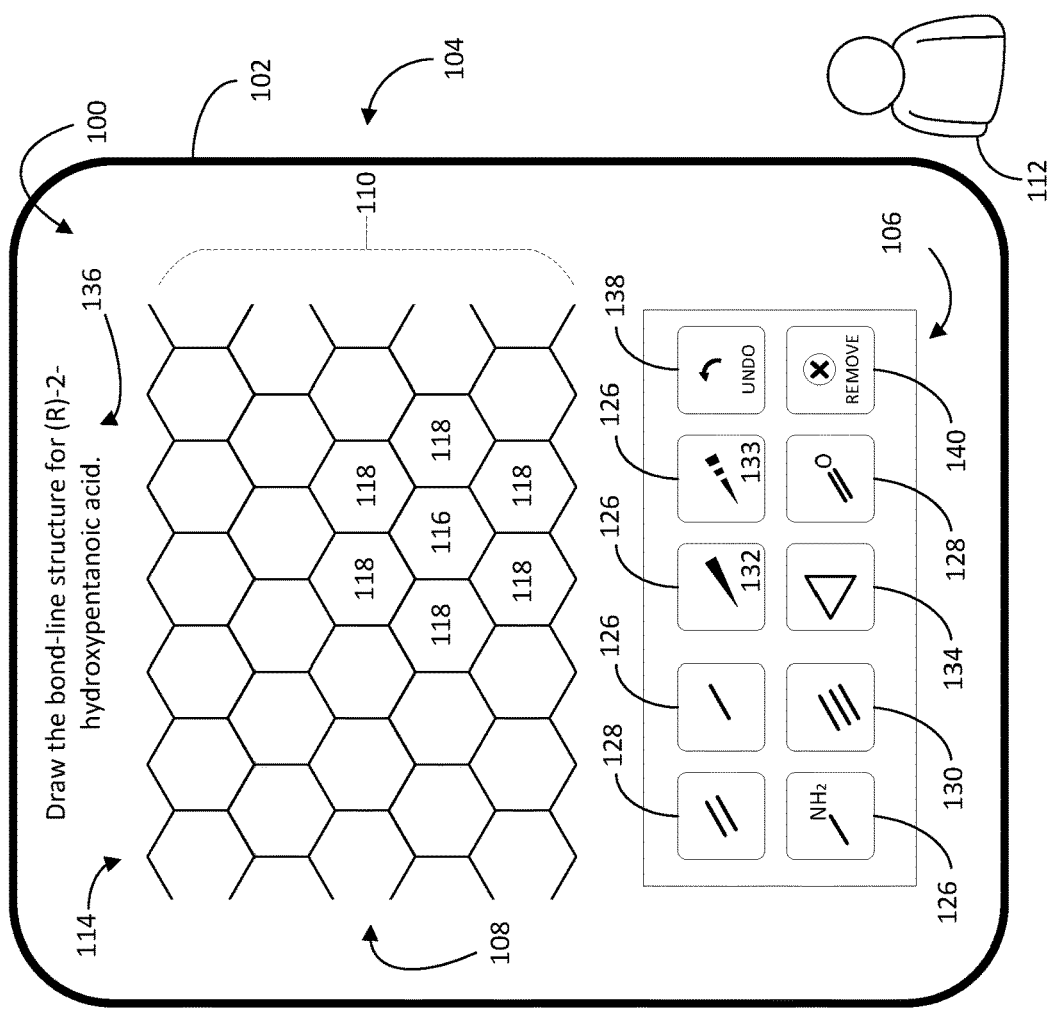
FIG. 1D
FIG. 1A

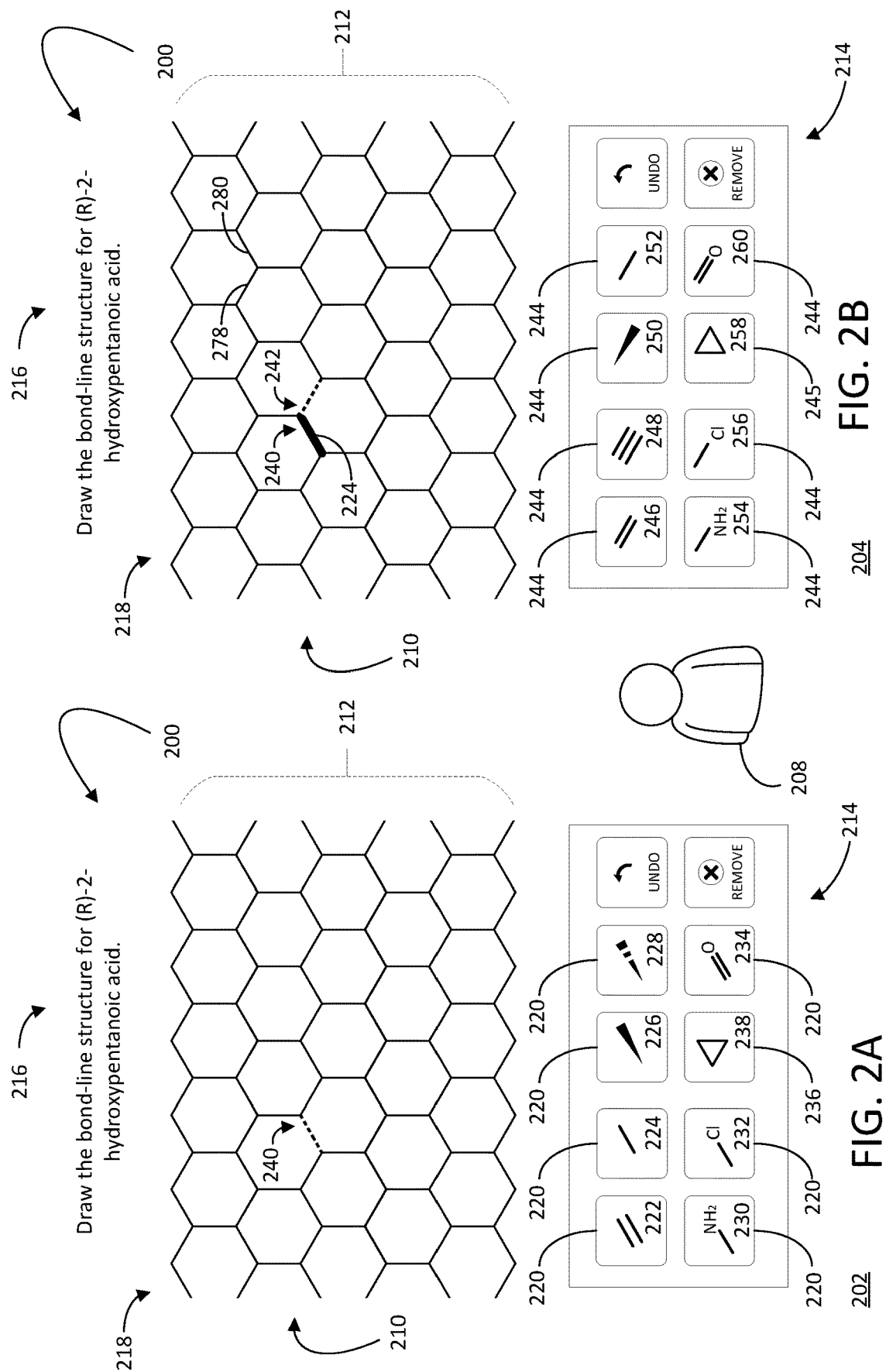

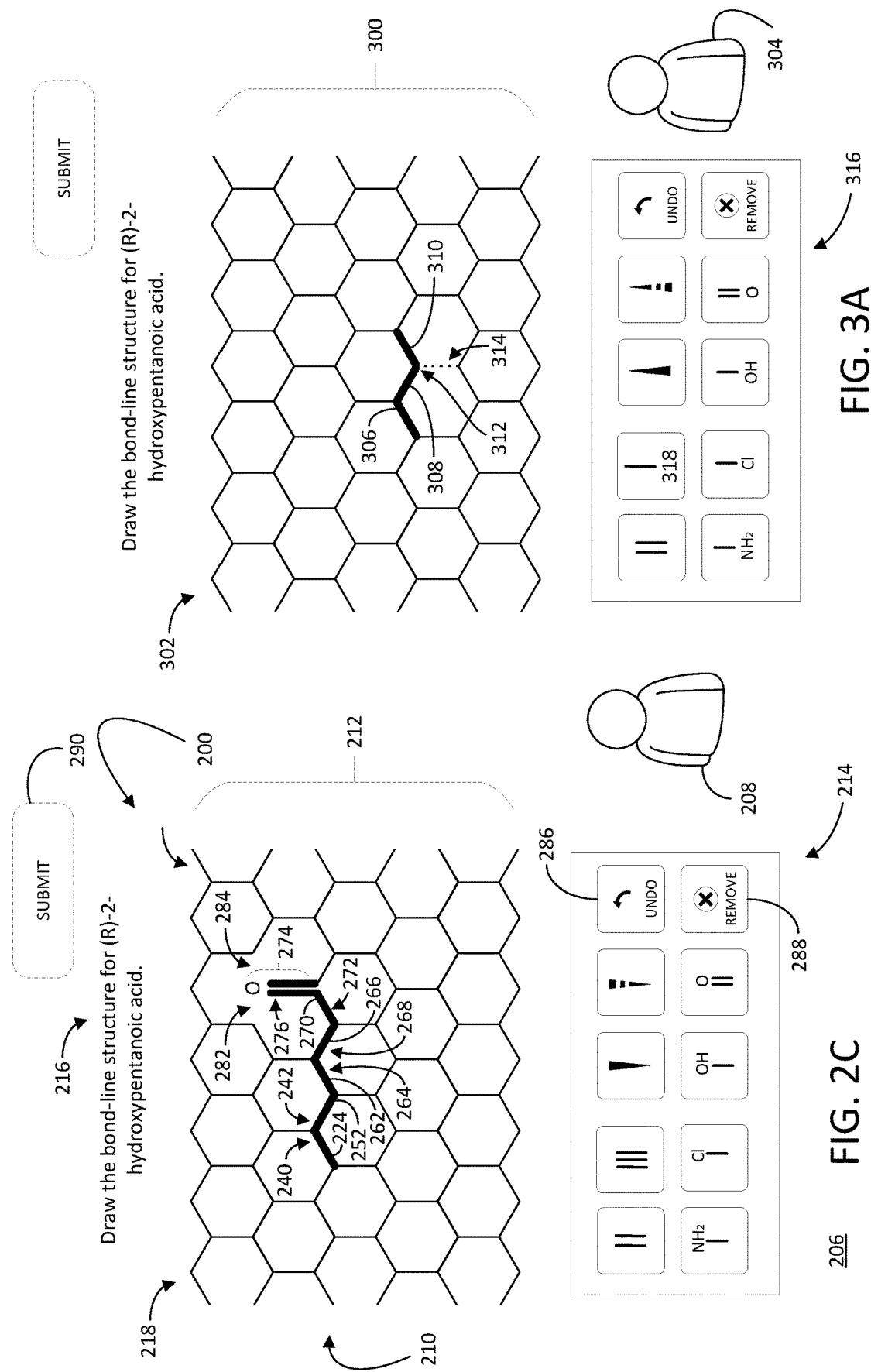

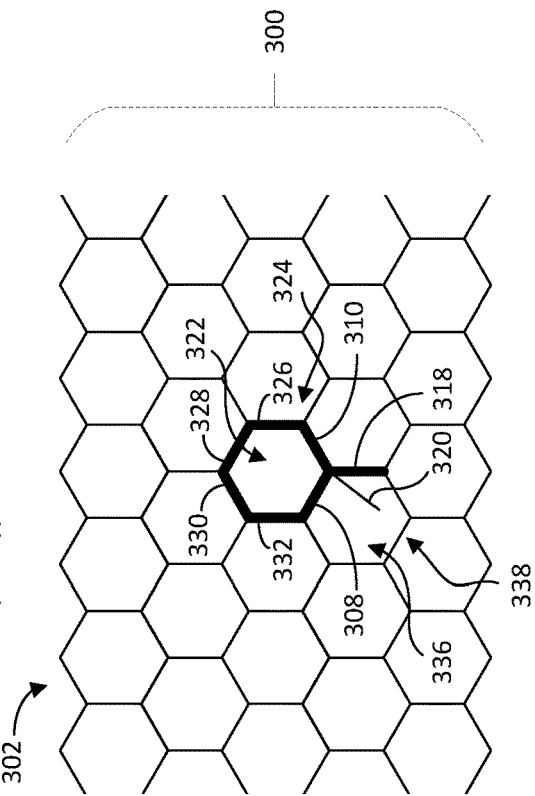
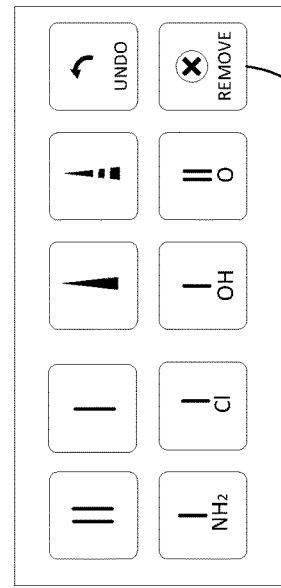
FIG. 3C
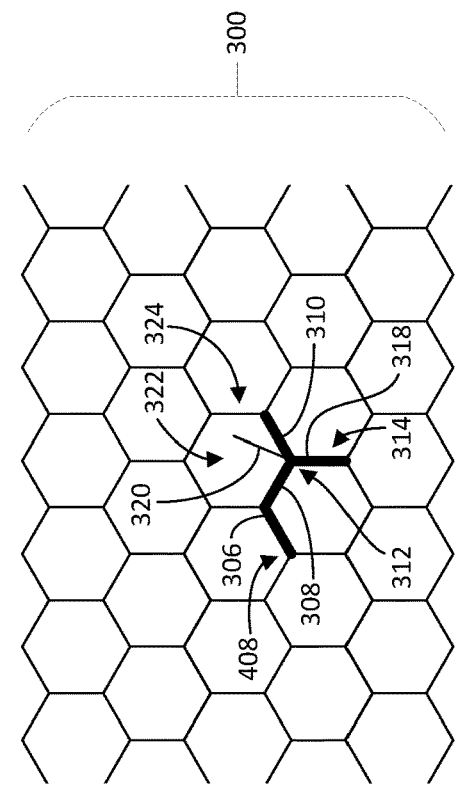
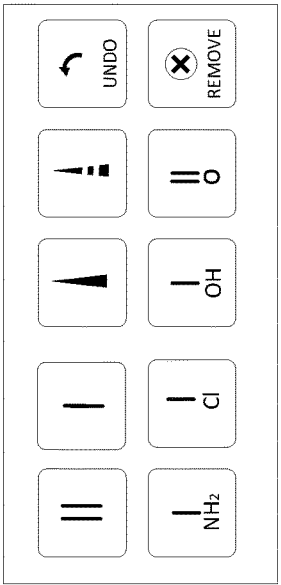
FIG. 3B

METHOD AND APPARATUS OF CHEMISTRY EDUCATION

FIELD OF TECHNOLOGY

An improved chemistry education system and method is disclosed. Improvements are applicable to the field of chemistry education.

BACKGROUND

In the field of chemistry education, computer applications that allow users to digitally "draw" chemical structures are often employed. These applications often serve as a general-purpose drawing tool. Further, such applications often operate under the assumption that the user knows how to draw the chemical structure they are tasked with drawing.

During operation, such applications often offer a menu of chemical structural components (e.g., chemical bond types, an atom type, functional group, and/or etc.) to the user. The user is generally then tasked with using these components to draw a chemical structure. In order to guide the user, the offered components are often components of the chemical structure the user is tasked with drawing. That is, structural components that are not part of the chemical structure the user is tasked with drawing are often not provided to the user. While this technique may allow the user to more quickly draw the chemical structure and reduce frustration, the student may not reap the benefits of experiential learning, where making and fixing mistakes often provides a more in depth learning experience.

Further, while such applications may minimize frustration a user may experience from making wrong decisions, the interface of these applications may actually increase frustration. For example, chemistry education applications may include an interface having application mechanics that rely heavily on drop-down windows and other cumbersome interfaces. These application mechanics may be frustrating to navigate.

Thus, there is a need for chemistry education systems and applications that maximize a user's learning potential while at the same time minimizing user frustration with the application mechanics.

BRIEF DESCRIPTION OF THE DRAWINGS

FIG. 1A-1D illustrates an exemplary chemistry education application and/or system operating on an exemplary computing device;

FIGS. 2A-2C illustrate exemplary operations of an exemplary chemistry education application and/or system at three different time points, respectively;

FIGS. 3A-3C illustrate the adaptive nature of an exemplary adaptive grid that may be employed by a chemistry education application and/or system;

DETAILED DESCRIPTION

Figure 4A:
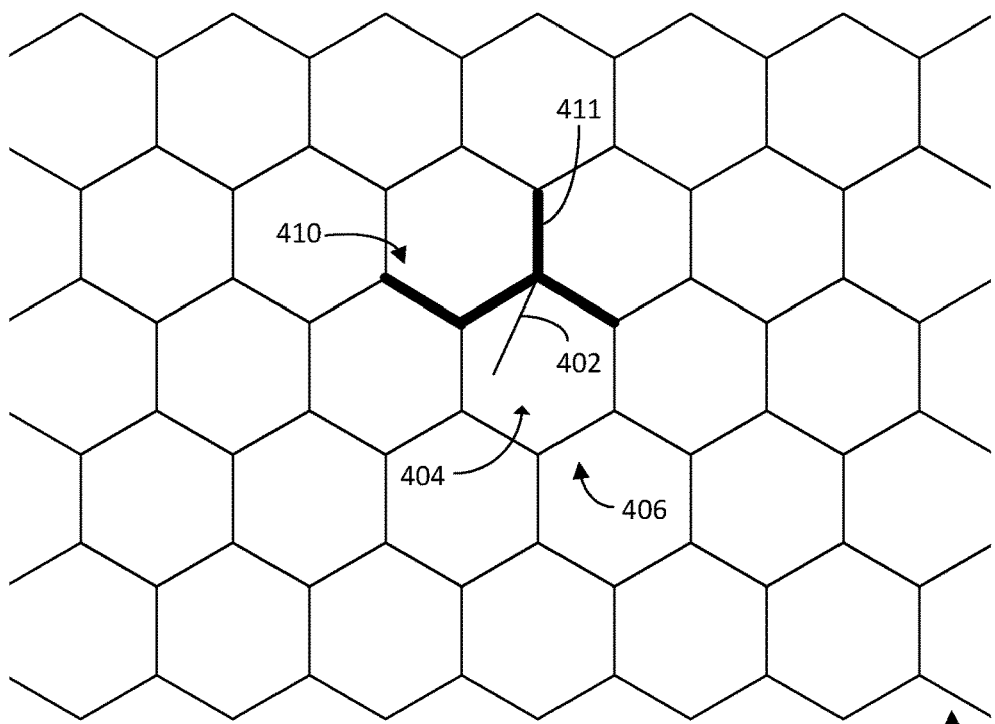
FIGS. 4A-4C illustrate further adaptive nature of an exemplary adaptive grid that may be employed by a chemistry education application and/or system.

FIG. 1A illustrates an exemplary chemistry system and/or application 100 (e.g., an organic chemistry education application) operating on a display 102 of a computing device 104 (e.g., a smart phone, computer tablet, a personal computer, or etc.). The chemistry application 100 presents a smart suggestion keyboard 106 on the display 102, as well as a drawing window 108. In the drawing window 108 is an adaptive molecule grid 110 (a.k.a., an adaptive grid) represented on the display 102. While the smart suggestion keyboard could be a physical keyboard, the smart suggestion keyboard 106 of FIG. 1A is a visual or virtual keyboard. As will be described in detail below, a user 112 selects a line on the adaptive grid 110 and then makes a selection from the smart suggestion keyboard 106 to be displayed at the selected line.

The adaptive grid 110 shown in FIG. 1A is an exemplary adaptive hexagon grid 114 including a plurality of conjoined hexagons, where at least one hexagon of the plurality of conjoined hexagons is conjoined with at least six adjacent hexagons of the plurality of conjoined hexagons. For example, a first hexagon 116 is conjoined with six adjacent hexagons 118.

Generally, and as shown in FIG. 1A, when the adaptive grid 110 is first displayed it is free of chemical bond lines. As will be discussed below, the adaptive grid 110 is effectively a skeletal grid or scaffold on which the user 112 creates a chemical structure.

In other examples, instead of the adaptive grid 110 being the adaptive hexagon grid 114 as shown in FIG. 1A, the adaptive grid 110 may instead include a different type of adaptive grid. For example, the adaptive grid 110 of FIG. 1A could instead include one or more of the following: an exemplary adaptive Fischer projection grid 120 including a skeleton of a molecular Fischer conformer (see, e.g., FIG. 1B); an exemplary adaptive Newman projection grid 122 including a skeleton of a molecular Newman conformer (see, e.g., FIG. 1C); or an exemplary adaptive chair projection grid 124 including a skeleton of a molecular chair conformer (see, e.g., FIG. 1D). Like the adaptive hexagon grid 114 of FIG. 1A, the exemplary adaptive grids 120-124 of FIGS. 1B-1D, respectively, are effectively skeletal grids or scaffolds on which the user 112 creates a chemical structure. Other exemplary adaptive grids will be discussed below with respect to FIGS. 5B-8B.

With reference back to FIG. 1A, the smart suggestion keyboard 106 includes a plurality of atomic bond representations associated either with a single atom or functional group. The plurality of atomic bond representations include one or more representations of a single covalent bond 126, a double covalent bond 128, and a triple covalent bond 130.

The single covalent bond representation may also include a wedge bond 132 and/or dash bond 133.

As illustrated in FIG. 1A, the plurality of atomic bond representations includes seven (7) atomic bond representations 126-130 associated either with a single atom or functional group. Other examples, however, may include more or less than the seven of these types of atomic bond representations. As will be appreciated, it is implicit that representations of bond types that do not include one or more atomic symbols are generally associated with a carbon atom.

In addition to the atomic bond representations 126-130 associated either with a single atom or functional group, the smart suggestion keyboard 106 may also include other types of molecular structure representations and/or simply atomic symbols. For example, the smart suggestion keyboard 106 may also include one or more ring extension molecular structures (e.g., a three-atom carbon ring extension 134). In other words, while the atomic bond representations 126-130 may be free of ring extension representations, the keyboard 106 may still include one or more a ring extension molecular structures (e.g., the three-atom carbon ring extension 134). Later examples will illustrate that a smart suggestion keyboard may also simply include chemical symbols (e.g., H, Cl, and $NH_2$) without representations of bond types (e.g., single covalent bond, double covalent bond, or triple covalent bond).

With continued reference to FIG. 1A, the chemistry application 100 may also provide a prompt 136 to the user 112, which may serve as a directive to the user 112. For example, the exemplary prompt 136 of FIG. 1A directs the user 112 to draw the bond-line structure for (R)-2-hydroxypentanoic acid." As will be described below, the user 112 uses a smart suggestion keyboard (e.g., smart suggestion keyboard 106) and a drawing window (e.g., drawing window 108) to create a proposed chemical structure on an adaptive grid (e.g., one of the adaptive grids of 110 of FIGS. 1A-1D) that is the same as the chemical structure set forth in the prompt 136. Further, as will be described below, the user 112 may employ an undo feature 138 and/or an remove feature 140 to aid in the creation of the proposed chemical structure.

With reference now to FIGS. 2A-2C, exemplary operation of a chemistry education system or application 200 is shown at three different time points 202-206 to illustrate a user 208 creating a proposed chemical structure in a drawing window 210. That is, FIG. 2A represents the first time point 202, FIG. 2B represents the second time point 204, and FIG. 2C represents the third time point 206. For the sake of simplicity, a computing device (e.g., the computing device 104 of FIG. 1A) on which the chemistry education system or application 200 may operate on is not shown.

As illustrated, the chemistry education application 200 of FIGS. 2A-2C includes an adaptive grid 212, a smart suggestion keyboard 214, and a prompt 216. The adaptive grid 212 in the present example is an exemplary adaptive hexagon grid 218 including a plurality of conjoined hexagons.

The exemplary prompt 216 of FIG. 2A directs the user 208 to "Draw bond-line structure for (R)-2-hydroxypentanoic acid" on the adaptive molecule grid 212. In other examples, however, a different prompt (i.e., a request to draw a different molecular structure) may be employed and a different adaptive molecule grid (e.g., adaptive molecule grids 120-124 of FIGS. 1B-1D) may be employed.

The smart suggestion keyboard 214 of FIG. 2A includes a first plurality of atomic bond representations 220 associated with a single atom or functional group. In the present example, this first plurality of atomic bond representations 220 associated with a single atom or functional group include the following: a double covalent carbon representation 222; a single covalent carbon bond representation 224; a single covalent carbon wedge bond representation 226 coming out of the display; a single covalent carbon dash bond 228 going into of the display; a single covalent $NH_2$ (i.e., a functional group) bond 230; a single covalent chlorine (Cl) bond 232; and a double covalent oxygen (O) bond 234. As discussed above, it is implicit that representations of bond types that do not include one or more atomic symbols (e.g., 222-228) are associated with a carbon atom.

The smart suggestion keyboard 214 also includes a ring extension 236. In the example illustrated in FIG. 2A, the ring extension 236 is a three-carbon ring extension 238. Unlike the first plurality of atomic bond representations 220 associated with a single atom or functional group, a ring extension (e.g., ring extension 236) is associated with more than one atom or functional group. For example, the three carbon ring extension 238 is associated with three carbon atoms, where each atom bonds to another atom.

While FIG. 2A illustrates a smart suggestion keyboard with eight (8) bond representations 222-234, 238, examples may include a smart suggestion keyboard with additional or fewer representations than those shown. Further, other examples may present bond types or representations different than those illustrated in FIG. 2A (i.e., the bond representations 222-234, 238).

With continued reference to FIG. 2A, and as mentioned above, the prompt 216 directs the user 208 to draw a chemical structure. In response to that prompt 216, the user 208 has selected a first location selection 240 on the adaptive grid 212, as represented at the first time point 202. While the user 208 may have selected any line of the adaptive molecule grid 212, the selection of the first location selection 240 is shown for exemplary purposes.

As illustrated in FIG. 2A, the selection 240 is highlighted with dashed line. Other highlighting techniques, however, may also be employed. For example, the selected line 240 could be shown in a color (e.g., red) different than the remainder of the adaptive molecule grid 212.

The user 208 can select a line (e.g., the first location selection 240) on the adaptive grid 212 by, for example, a touch such as a tap or press on the line with a finger or stylus. Other selection techniques, however, may instead be employed. For example, if a computer mouse or other type pointer moving device is employed, the user 208 can use that device to cause a pointer or cursor to be moved to the first location selection 240 for selection.

Once the first line 240 is selected, each bond representation 222-234 of the first plurality atomic bond representations 220 associated with a single atom or functional group is oriented in a direction that is substantially parallel to the first selected line 240. The substantially parallel orientation of the first location selection 240 with each of the first plurality atomic bond representations 220 associated with a single atom or functional group may serve as a visual cue so that the user 208 knows that a location on the adaptive grid 212 has been properly selected. In some examples, as shown in FIG. 2A, any ring extension (e.g., three-carbon ring extension 238) that may be represented on the keyboard 214 may also be oriented such that at least one side of the ring extension is substantially parallel to the selected location (e.g., location 240).

Once the user 208 has made a selection (e.g., the first location selection 240) on the adaptive grid 212, the user 208 may make a bond selection from the smart suggestion keyboard 214. That is, the user 208 may select one of the bond types 222-234, 238 from the smart suggestion keyboard 214. The bond selection will then be placed at the first location selection 240 on the adaptive grid 212. As with making a selection on the adaptive grid 212, the user 208 may make a selection from the smart suggestion keyboard 214 by either touching the selection or by using a pointing device (e.g., a mouse or stylus) to make the selection.

If, for example, the user selects the single covalent $NH_2$ 230 on the smart suggestion keyboard 214, the single covalent $NH_2$ bond 230 will be placed at the first location selection 240. Not every bond type selection, however, is a correct or feasible selection in light of the prompt 216. For example, the exemplary prompt 216 of FIG. 2A directs the user 208 to "Draw the bond-line structure for (R)-2-hydroxypentanoic acid." The bond-line structure of (R)-2-hydroxypentanoic acid, however, does not include an $NH_2$ functional group. As such, the (R)-2-hydroxypentanoic acid does not include the single covalent $NH_2$ bond 230. Accordingly, the single covalent $NH_2$ bond 230 would be an incorrect selection. Nonetheless, the user 208 is allowed to select the single covalent $NH_2$ bond 230 to be placed at the first location selection 240 if the user chooses to do so. By allowing the user 208 to make mistakes, the user 208 is allowed to take part in experiential learning which may provide longer term retention benefits.

For purpose of the exemplary situation represented in FIGS. 2A-2C, instead of selecting the single covalent $NH_2$ bond 230, the user 208 selected the single covalent carbon bond 224 from the smart suggestion keyboard 214 of FIG. 2A to be placed at the first location selection 240 as shown in FIG. 2B. That is, after the user 208 selected a first atomic bond type (i.e., selection 224) from the keyboard 214, the selection 224 is presented at the first location selection 240 as shown in FIG. 2B.

In addition to illustrating that the user 208 has selected the first atomic bond selection (i.e., the single covalent bond of carbon 224 of FIG. 2A) for the first location selection 240 shown in FIG. 2B, the second time point 204 represented in FIG. 2B also illustrates that the user has selected a second location selection 242 on the adaptive grid 212. Once the second location 242 is selected, the previously offered selections 222-234, 238 of FIG. 2A are no longer displayed. Instead, a second plurality of atomic bond representations 244 (FIG. 2B) associated with a single atom or functional group is displayed on the smart suggestion keyboard 214. Further, a ring extension 245 is also displayed on the smart suggestion keyboard 214. In other words, the second plurality of atomic bond representations 244, 245 replaces the first plurality of atomic bond representations 220, 236 after the user 208 has made the second location selection 242.

Further, each atomic bond representation 246-256, 260 associated with one atom or functional group of the second plurality of atomic bond representations 244 is oriented such that each is substantially parallel to the second location selection 242. Similar to FIG. 2A, the substantially parallel orientation of the second location selection 242 of FIG. 2B with the second plurality atomic bond representations 244 serves as a visual cue to the user 208 that a location on the adaptive grid 212 has been properly selected. In some examples, as shown in FIG. 2B, any ring extension (e.g., three-carbon ring extension 258) that may be present on the keyboard 214 may be oriented such that at least one side of the ring extension is substantially parallel to the selected location (e.g., location 242).

While some of the selections of the smart selection keyboard 214 of FIG. 2A are similar to the selections of the smart suggestion keyboard 214 of FIG. 2B (e.g., compare selection 230 of FIG. 2A with selection 254 of FIG. 2B), in other examples they may be different. That is, bond types not shown in either FIG. 2A or 2B may also, or instead, be employed. For example, while the keyboard 214 of FIG. 2A includes a three carbon ring extension 238 as does the keyboard 214 of FIG. 2B (see three carbon ring extension 258), other examples may not include ring extensions 238, 258 or include different ring extension(s).

With continued reference to FIG. 2B, once the user 208 has selected the second location 242, the user can then make a selection (e.g., the single covalent carbon bond 252) from the smart suggestion keyboard 214 of FIG. 2B to serve as an atomic bond selection for the second selected line 242 on the adaptive grid 212, which is illustrated at the third time point 206 of FIG. 2C.

Examples set forth herein illustrate that a grid line may be selected (e.g., the first or second selections 240, 242, respectively) by the user and then a respective input form the keyboard (e.g., smart selection keyboard 214) may be selected by the user to appear on the adaptive grid (e.g., the adaptive hexagon grid 218) at the selected grid location. In other examples, however, a default single covalent bond may appear at the selected grid location without the user selecting an input from the keyboard (e.g., the smart selection keyboard 214). That is, when the user selects a grid line, a single covalent bond may automatically be placed at that selected grid location. Single covalent bonds (e.g., a single covalent carbon bond) in, for example, organic chemistry are often employed to build chemical structures. As such, defaulting to a single covalent bond may save user time. In such examples, where a single covalent bond is defaulted to the selected location, the user 208 may still be given the opportunity to make a different selection from the keyboard 214 to replace the defaulted single covalent bond. Further details regarding the aforementioned exemplary default bonds are set forth below with respect to FIGS. 9A-9B.

With reference now to FIG. 2C, additional exemplary user inputs or selections are shown displayed on the adaptive grid 212. That is, the user has caused the selection of a third single covalent carbon bond 262 to be represented at a third location 264, a fourth single covalent carbon bond 266 at a fourth location 268, a fifth single covalent bond 270 at a fifth location 272, and a double covalent oxygen (O) bond 274 at a sixth location 276. The additional bond selections 262, 266, 270, 274 were selected in much the same manner as previously described, but at time points not shown.

The selection of the double covalent oxygen bond 274 at the sixth location selection 276 illustrates an adaptive nature of the adaptive grid 212. For example, once the double covalent oxygen bond 274 is placed on the adaptive molecule grid 212, the adaptive grid 212 is adapted to remove a first unused grid line (a.k.a., first extension line 278 of FIG. 2B) and a second unused grid line (a.k.a. second extension line 280 of FIG. 2B). Accordingly, the user 208 cannot add structure to these two regions (282, 284) shown in FIG. 2C. In other words, the double covalent oxygen (O) bond 274 serves as a terminal grid point in which no further bond structure can be added thereto by the user 208.

Other terminal grid points causing the removal of grid line(s) may arise if, for example, a wedge bond or a double covalent chlorine (Cl), bromine (Br), fluorine (F), hydrogen (H), or magnesium (Mg) bond is added to the adaptive grid 212. The implementation of terminal grid points illustrates the adaptive nature of the grid 212. Further, implementations of terminal grid point(s) may occur in other situations not discussed. That is, the listing above of terminal endpoints causing the removal of grid line(s) is non-exhaustive.

As previously mentioned, the user 208 is allowed to make mistakes as they attempt to create the chemical structure on the adaptive grid 212. The implementation of terminal grid points to remove grid structure (e.g., the first and second extension lines 278, 280 of FIG. 2B), however, at least partially directs the user away from making mistakes that are chemically infeasible such as a carbon atom with five (5) or more bonds, thus potentially easing user frustration.

While the implementation of terminal grid points may direct the user 208 away from making some mistakes, the user 208 is not stopped from making many other mistakes. To give the user 208 the opportunity to correct mistakes, the smart suggestion keyboard 214 may include an undo function 286 and/or a remove function 288. By the selecting the undo function 286, the user 208 may remove the last bond presented on the adaptive grid 212. Alternatively, the user 208 may select any input already on the adaptive grid 212 (e.g., one of bond selections 224, 252, 262, 266, 270, 274) and employ the remove function 288 to remove the selected bond input form the adaptive grid 212. If desired, the user 208 may employ the keyboard 214 in much the same manner discussed above to input a different bond representation onto the grid 212.

Once the user 208 is finished creating the proposed structure, the user may select a submit function 290. Once selected, the chemistry education application 200 determines if the user created chemical structure is equivalent to the chemical structure set forth in the prompt 216. If the structures are not equivalent, the user 208 may, for example, add new bond(s), employ the undo function 286, and/or employ the remove function 288 to attempt to correct their created chemical structure. Further, while the chemistry education application 200 may notify the user 208 that the user created chemical structure is not accurate, the chemistry education application 200 may simply offer hints about how to correct the user created chemical structure. That is, the chemistry education application 200 need not notify the user 208 as to what particular bond selections (e.g., one or more of bond selections 224, 252, 262, 266, 270, 274) or not accurate. Instead, the chemistry education application 200 may simply notify the user 208 that the user created structure is not accurate or provide hints to guide the user 208 to the correct solution/structure.

Before continuing to FIGS. 3A-3C, it is noted that, while inputs 224, 252, 262, 266, 270, 274 are represented as being selected by the user 208, they need not be. For example, with reference to FIGS. 2A and 2B, instead of the chemistry education application 200 initially presenting the user 208 the adaptive grid 212 free of bond representations or lines (e.g., FIG. 2A), the chemistry education application 200 may initially present the adaptive grid 212 with one or more bond representations already presented thereon. That is, the initial adaptive grid (e.g., adaptive hexagon grid 218) may be presented to the user with one or more bond representations already shown or preloaded thereon. For example, FIG. 2B could serve as the initial hexagon grid 218 having the single covalent bond 224 preloaded on the gird 218. Other examples, may include additional or different bond representations preloaded on the grid 212.

The ability to preload bond representation(s) onto the adaptive grid may serve a variety of purposes. For example, preloaded bond representation(s) may ease the user's task of creating the chemical structure set forth in the prompt. Alternatively, a preloaded adaptive grid may include an inaccurate chemical structure(s) thereon and the prompt may direct the user to correct the preloaded chemical structure(s). The chemistry education application 200 may employ this strategy to, for example, help the user identify common mistakes. To correct the preloaded structure, the user may employ functionality already described above (e.g., utilizing the undo 286 or remove 288 functions).

Referring now to FIGS. 3A-3C, additional examples of the adaptive nature of an adaptive grid 300 are illustrated. The adaptive grids 300 illustrated are adaptive hexagon grids 302.

With reference to FIG. 3A, an exemplary situation is illustrated where a user 304 has already created a carbon atom having three single covalent bonds (i.e., a first, second, and third covalent carbon bond 306, 308, 310, respectively) coupled thereto. As discussed above, where two or more bonds meet at a node (e.g., node 312), and where no atomic symbol is present, it is understood that a carbon atom is at that node (e.g., node 312).

FIG. 3A also illustrates that the user 304 has selected a next location selection 314 on the adaptive hexagon grid 302 and is ready to make a selection from a smart suggestion keyboard 316. As mentioned above, the situation illustrated in in FIG. 3A is merely exemplary. In other examples the user may have selected different bond selections and/or grid locations. Further, as discussed above with respect to FIGS. 2A-2C, in some examples a grid selection (e.g., location selection 314) may cause a default single covalent bond to be presented at that selected location.

Nonetheless, with reference to both FIGS. 3A and 3B, where exemplary default bonds are not employed, it is seen that the user 304 has selected a first single covalent bond 318 from the smart suggestion keyboard 316 of FIG. 3A to be input at the first location selection 314 on the adaptive hexagon grid 302 of FIG. 3B. Accordingly, as illustrated in FIG. 3B, three covalent bonds 308, 310, 312 stem from the carbon atom at the node 312.

After a structure having three single covalent bonds (e.g., bonds 308, 310, 318) coupled to a node (e.g., node 312) is created by the user 304, an appended grid line 320 stemming from the node 312 may be added. The appended grid line 320 is shown at an interior location 322 of a first hexagon 324 of the adaptive hexagon grid 302. Accordingly, the user 304 is offered the opportunity to select the appended grid line 320 in order to add a fourth bond to the node 312.

There is no requirement, however, that the user 304 input a bond to the appended grid line 320. Nonetheless, FIG. 3B illustrates that an appended grid line may be added to an adaptive grid when three single covalent bonds meet at a node. That is, the appended grid line 320 is presented on the adaptive hexagonal grid 302 after the user 304 has caused a set of three atomic bond representations (i.e., bond representations 308, 310, 318) to appear on the adaptive hexagonal grid 302 such that the set of three atomic bond representations 308, 310, 318 meet at a node (e.g., node 312). A node (e.g., node 312) is where two or more lines of the adaptive hexagon grid (e.g., adaptive grid 302) meet.

While FIG. 3B illustrates the implementation of adding an appended grid line (e.g., appended grid line 320), the user 304 may also cause the removal of the appended grid line 320. For example, if the single covalent bond of 308 were replaced with a double covalent bond, the appended grid line 320 would be removed. Other examples may also cause the addition or removal of appended grid line(s).

FIG. 3C illustrates an example where the user 304 chose not to input a bond at the interior location 322 of the hexagon 324. Rather, the user 304 proceeded to add additional bonds 326, 328, 330, 332 around the hexagon 324, thus creating a six-membered carbon ring (308, 310, 326, 328, 330, 332). The bond selections were made in much the same manner as described above, and at time points not shown. The user 304 has also employed a remove function 334 to remove the single covalent carbon bond 306 represented in FIG. 2B (compare FIG. 2B with FIG. 2C).

The creation of the six-member ring (308, 310, 326, 328, 330, 332) caused the appended grid line 320 to move from the interior location 322 of the first hexagon 324 (FIG. 4B) to an interior location 336 of a second hexagon 338 (FIG. 4C) of the adaptive hexagon grid 400. As such, the appended grid line 320 does not appear inside a six-membered chemical ring (e.g., the ring comprised of bonds 308, 310, 326, 328, 330, 332) since that would create a chemically infeasible structure.

Figure 4B:
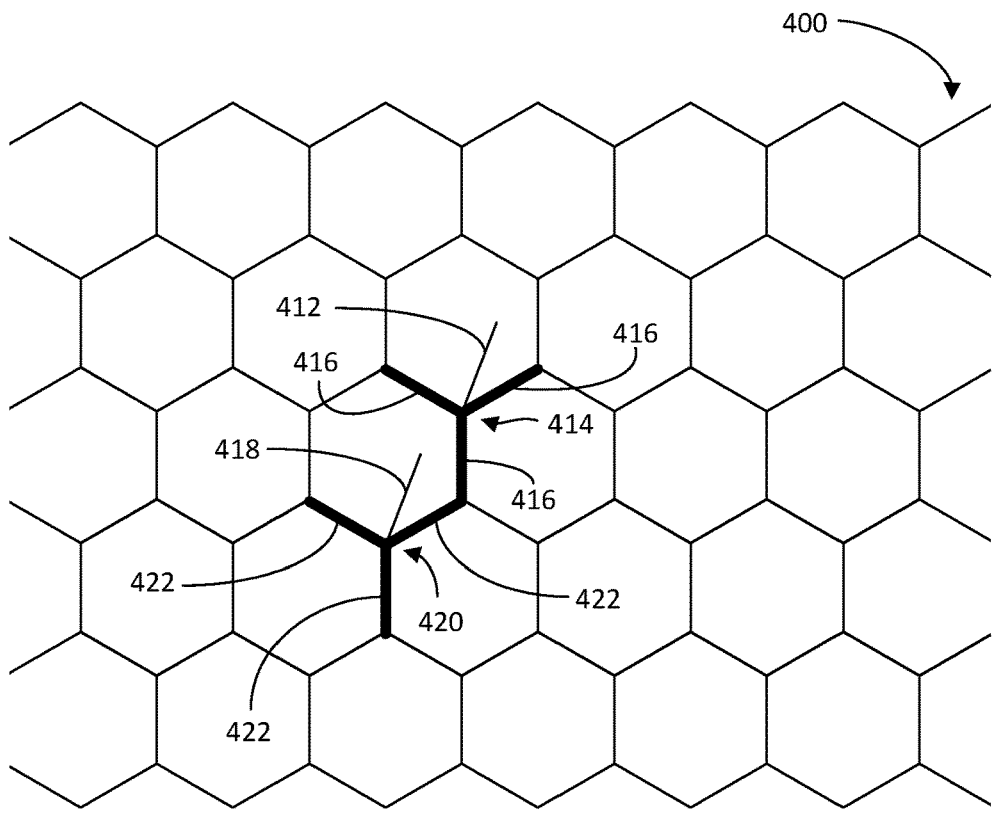
Figure 4C:
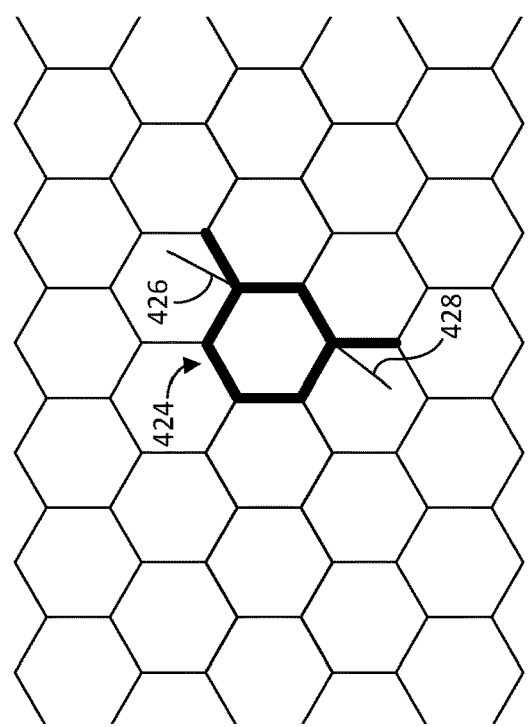

Proceeding to FIGS. 4A through 4C, other examples where appended lines may be added to an adaptive hexagonal grid 400 are illustrated. For simplicity, no smart suggestion keyboard is shown. FIG. 4A illustrates an appended grid line 402 at an interior location 404 of a first hexagon 406 of the adaptive hexagon grid 400.

A comparison of FIGS. 4A and 3B illustrates two exemplary types of structures where appended grid lines may arise. The structure in FIG. 3B is a concave linear structure 408 and the structure illustrated in FIG. 4A is a convex linear structure 410. Each appended grid line 320, 402 appears generally opposite the respective vertical bond line (i.e., bond line 411 of FIG. 4A and bond line 318 of FIG. 3B).

FIGS. 4B and 4C illustrate yet further examples where appended grid lines may be employed. For example, FIG. 4B illustrates a first appended grid line 412 stemming from a first node 414 of a first set of three bond lines 416 and a second appended grid line 418 stemming from a second node 420 of a second set of three bond lines 422.

FIG. 4C illustrates appended grid lines stemming from a six-membered ring 424. That is, a first appended grid line 426 was added to the six-membered ring 424 as well as a second appended grid line 428.

Figure 5A:
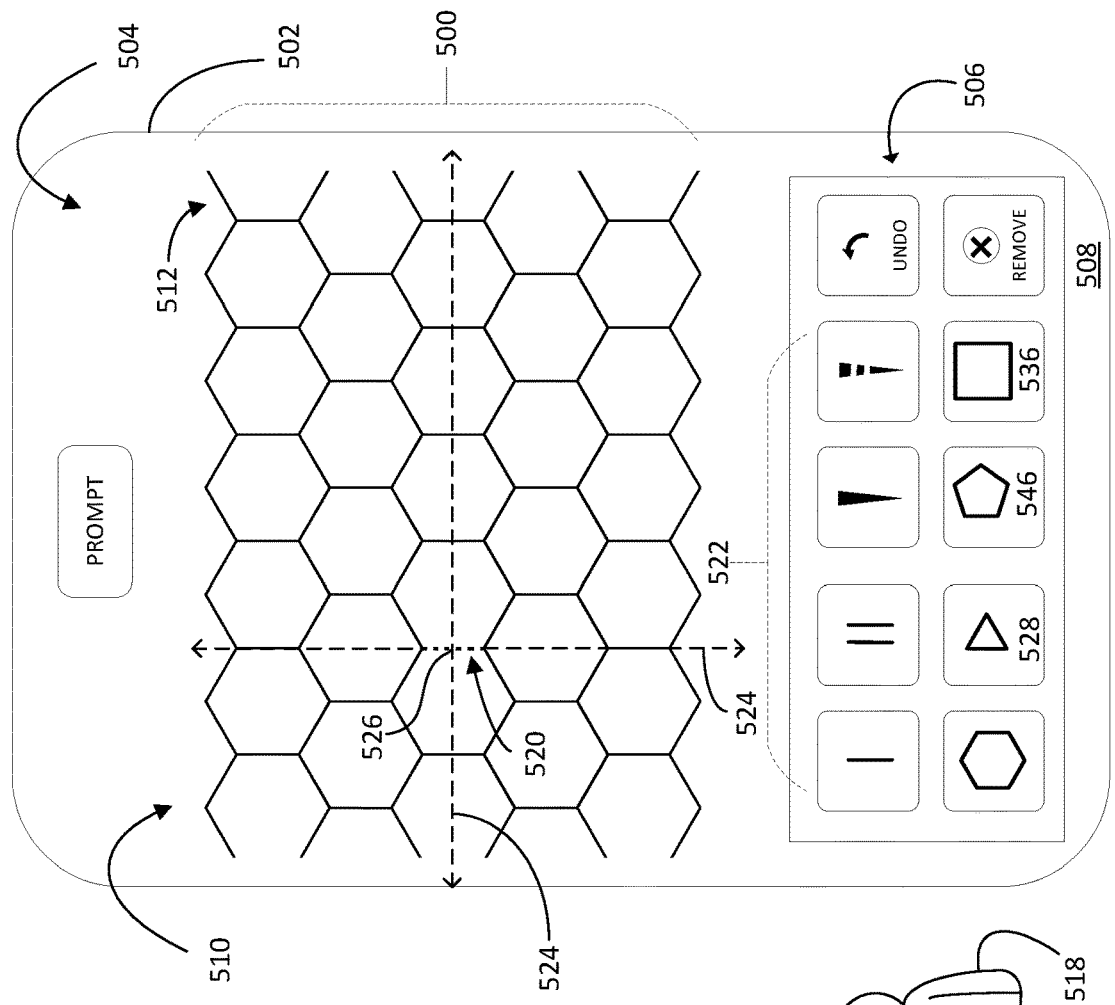
FIGS. 5A-5D illustrate exemplary situations in which exemplary adaptive grids of a chemistry education application and/or system may be manipulated.

With reference now to FIGS. 5A-5D, additional exemplary situations where an adaptive grid 500 may be manipulated are illustrated. Referring to FIG. 5A, an exemplary computing device 502 having an exemplary chemistry education application 504 operating thereon is shown. The chemistry education application 504 presents the adaptive grid 500 and an exemplary smart suggestion keyboard 506 on a display 508. The adaptive grid 500 illustrated in FIG. 5 is an exemplary adaptive hexagon grid 510.

Figure 5C:
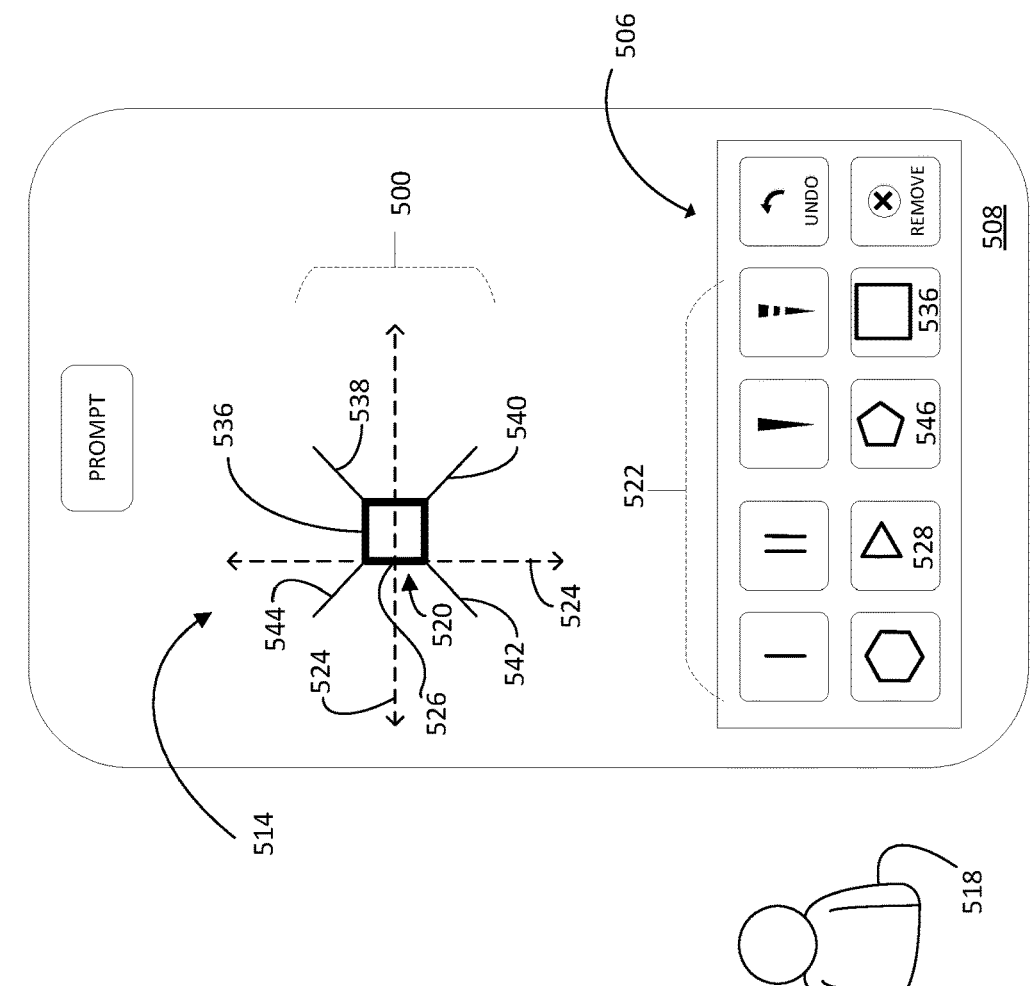
Figure 5B:
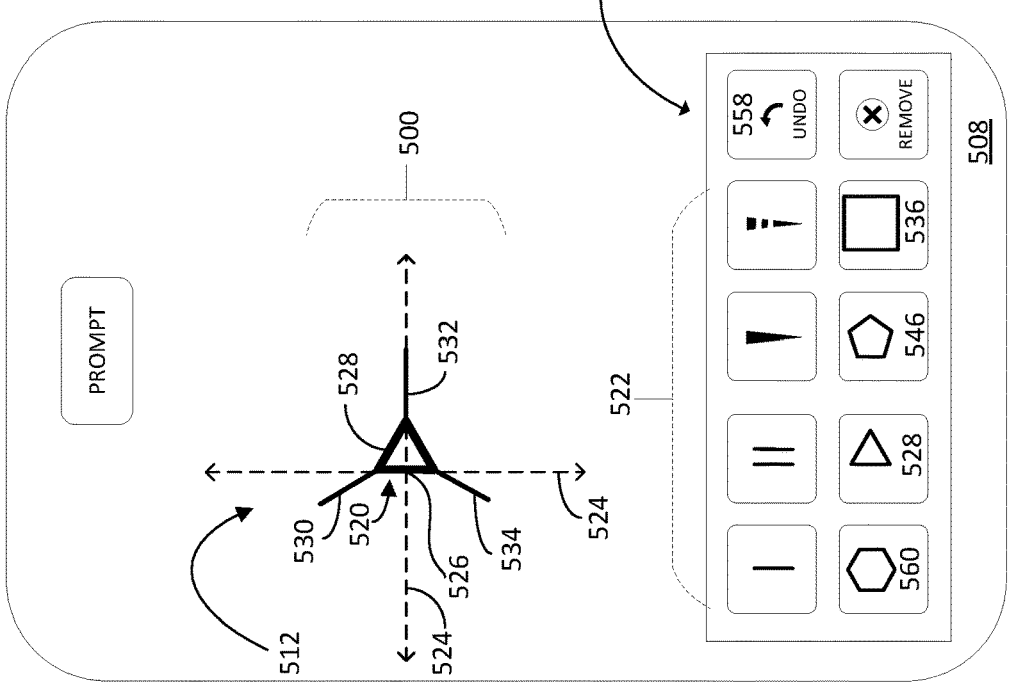
Figure 5D:
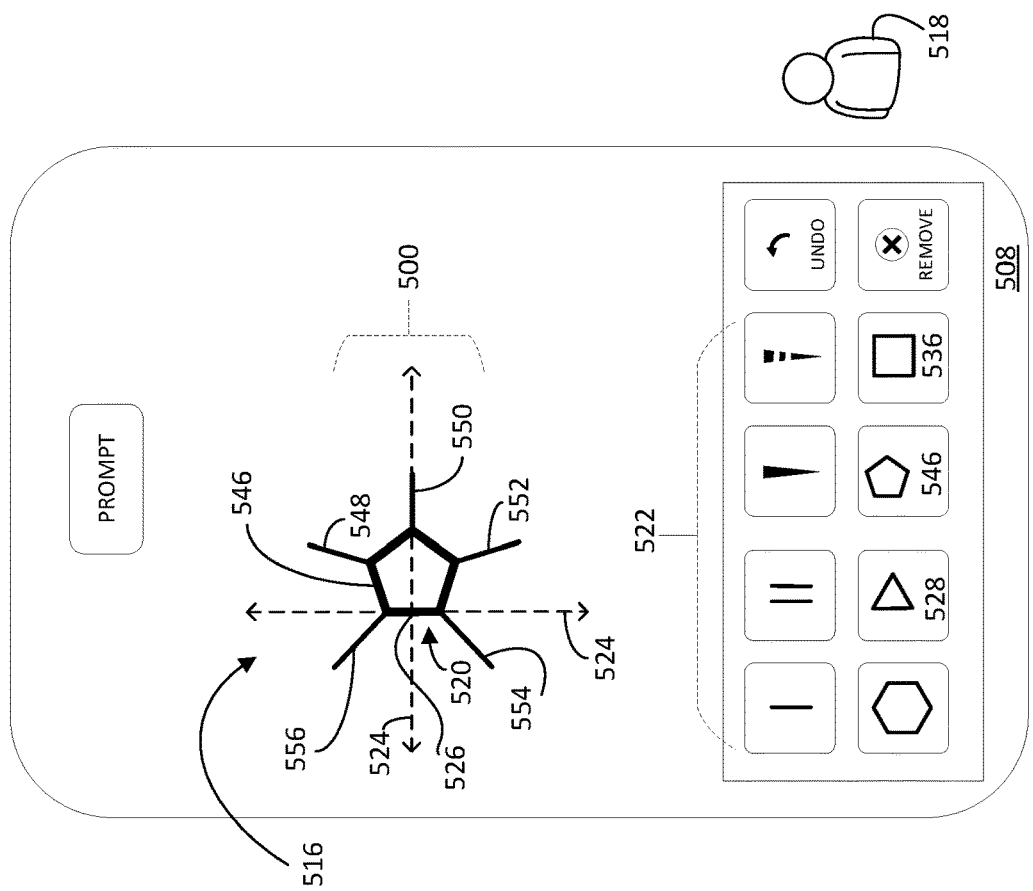

FIGS. 5B-5D illustrate additional exemplary adaptive grids 500. The adaptive grid 500 of FIG. 5B is an adaptive triangle extension grid 512, the adaptive grid 500 of FIG. 5C is an adaptive square extension grid 514, and the adaptive grid 500 of FIG. 5D is an adaptive pentagon extension grid 516.

Referring back to the exemplary situation illustrated in FIG. 5A, a user 518 has selected a first location selection 520 (i.e., has selected a grid line) on the adaptive hexagon grid 510 and is provided a plurality of inputs 522 from an exemplary smart suggestion keyboard 506.

A pair of orthogonal axes 524 are shown for illustrative purposes. That is, the orthogonal axes 524 are not represented on the display 508. The two orthogonal axes 524 cross each other at a location (i.e., a display location 526) on the display 508. The display location 522 generally bisects the first location selection 520.

Moving from FIG. 5A to FIG. 5B, after selecting the first location selection 520 from the exemplary adaptive hexagon grid 510, the user 518 selected a three-carbon extension ring 528 from the smart suggestion keyboard 506 of FIG. 5A. As such, the three-carbon extension ring 528 is presented on the adaptive triangle extension grid 512 of FIG. 5B at the first location selection 520. As represented by the display location 526 of FIGS. 5A and 5B, the first location selection 520 of FIG. 5A is at substantially the same location on the display 508 as the first location selection 520 illustrated in FIG. 5B.

As illustrated in FIGS. 5A-5B, after the three-carbon extension ring 528 has been selected, the adaptive hexagon grid 510 of FIG. 5A transitioned to the adaptive triangle extension grid 512 of FIG. 5B. In other words, the adaptive hexagon grid 510 of FIG. 5A has transformed into the adaptive triangle extension grid 512 of FIG. 5B.

After transitioning, three potential selection lines 530, 532, 534 remain as shown in FIG. 5B. The user 518 may employ the smart suggestion keyboard 506 to add atomic structural components to one or more of the three potential selection lines 530-534. In much the same manner describe above with respect to FIGS. 1A-2C, the plurality of inputs 522 and their orientation on the smart suggestion keyboard 506 may change depending on the grid line 530-534 selected by the user 518.

FIGS. 5A and 5C represent another exemplary situation that illustrates the adaptive nature of the adaptive molecule grid 500. Instead of selecting the three-carbon extension ring 528 as illustrated in FIG. 5B, FIG. 5C illustrates that the user 518 has selected a four-carbon extension ring 536 from the keyboard 506 of FIG. 5A to be presented at the first location selection 520 of FIG. 5C. Accordingly, the adaptive hexagon grid 510 of FIG. 5A has been modified to the adaptive square extension grid 514 of FIG. 5C. As represented by the display location 526 of FIGS. 5A and 5C, the first location selection 520 of FIG. 5A is at substantially the same location on the display 508 as the first location selection 520 illustrated in FIG. 5C.

With continued reference to FIG. 5C, the adaptive square extension grid 514 includes four potential selection lines 538, 540, 542, 544 (a.k.a., grid lines) extending from each vertex of the four-carbon extension ring 536. The user 518 may employ the smart suggestion keyboard 506 to add atomic structural components to one or more of the four potential selection lines 538-544. In much the same manner describe above with respect to FIGS. 1A-2C, the plurality of inputs 522 and their orientation on the smart suggestion keyboard 506 may change depending on the grid line 538-544 selected by the user 518.

FIGS. 5A and 5D represent yet another exemplary situation that illustrates the adaptive nature of the adaptive molecule grid 500. Instead of selecting either the three-carbon extension ring 528 or the four-carbon extension ring 536 as illustrated in FIGS. 5B and 5C, respectively, FIG. 5D illustrates that the user 518 selected a five-carbon extension ring 546 (a.k.a., a pentagon extension ring) from the keyboard 506 of FIG. 5A to be presented at the first location selection 520 of FIG. 5D. Accordingly, the adaptive hexagon grid 510 of FIG. 5A transformed into the adaptive pentagon extension grid 516 of FIG. 5D. As represented by the display location 526 of FIGS. 5A and 5D, the first location selection 520 of FIG. 5A is at substantially the same location on the display 508 as the first location selection 520 illustrated in FIG. 5D.

Still referring to FIG. 5D, the adaptive pentagon extension grid 516 includes five potential selection lines 548, 550, 552, 554, 556 extending from each vertex of the five-carbon extension ring 546. The user 518 may employ the smart suggestion keyboard 506 to add atomic structural components to one or more of the five potential selection lines 548-556. In much the same manner describe above with respect to FIGS. 1A-2C, the plurality of inputs 522 and their orientation on the smart suggestion keyboard 506 may change depending on the grid line 548-556 selected by the user 518.

With reference now to FIGS. 5A-5D, the display point or location 526 defined by the pair of orthogonal axes 524 illustrates that, at least in some examples, the first location selection 520 of each adaptive grid 510-516 is generally at the same location (i.e., the display point 526) on the display 508. In other words, the first location 520 on each grid may be at the same location or position on the display. In other examples not shown, however, the first location selection 520 on each grid 510-516 need not be at the same location on the display 508.

While examples discussed above with respect to FIGS. 5A-5D illustrate the adaptation of the hexagon grid 510 to the grids 512-516 of FIG. 5B-5D, respectively, the grids may adapt in other ways. For example, the triangle extension grid 512 of FIG. 5B may adapt to the square extension grid 514 of FIG. 5C or the pentagon extension grid 516 of FIG. 5D. Similarly, the square extension grid 514 of FIG. 5C may adapt to the form of the triangle extension grid 512 of FIG. 5B or the pentagon extension grid 516 of FIG. 5D.

These transformations may be bi-directional. That is, any one of the grids 510-516 of FIGS. 5A-5D may transform into any other of the grids 510-516 of FIGS. 5A-5D. Such adaptations or transformations may be based on selections the user 518 makes from the smart suggestion keyboard 506. For example, with respect to FIG. 5B, the user 518 may select an undo function 558 from the keyboard 506 to cause the removal of the three-carbon ring extension 528 from the triangle extension grid 512. The user 518 may then re-select the first location selection 520 (or another selection) and then select a different extension ring (e.g., one of extension rings 536, 546, or 560) as an input for that location 520 (or other selected location), thus causing the associated grid to appear with the selected extension ring.

Lastly, while the exemplary selections available on the smart suggestion keyboard 506 are the same for each of FIGS. 5B-5D, they need not be. Further, while examples of 3, 4, and 5-membered rings have been illustrated, other examples may include greater membered rings (e.g., 7, 8, 9, or more) employed in much the same manner described above.

Figure 6A:
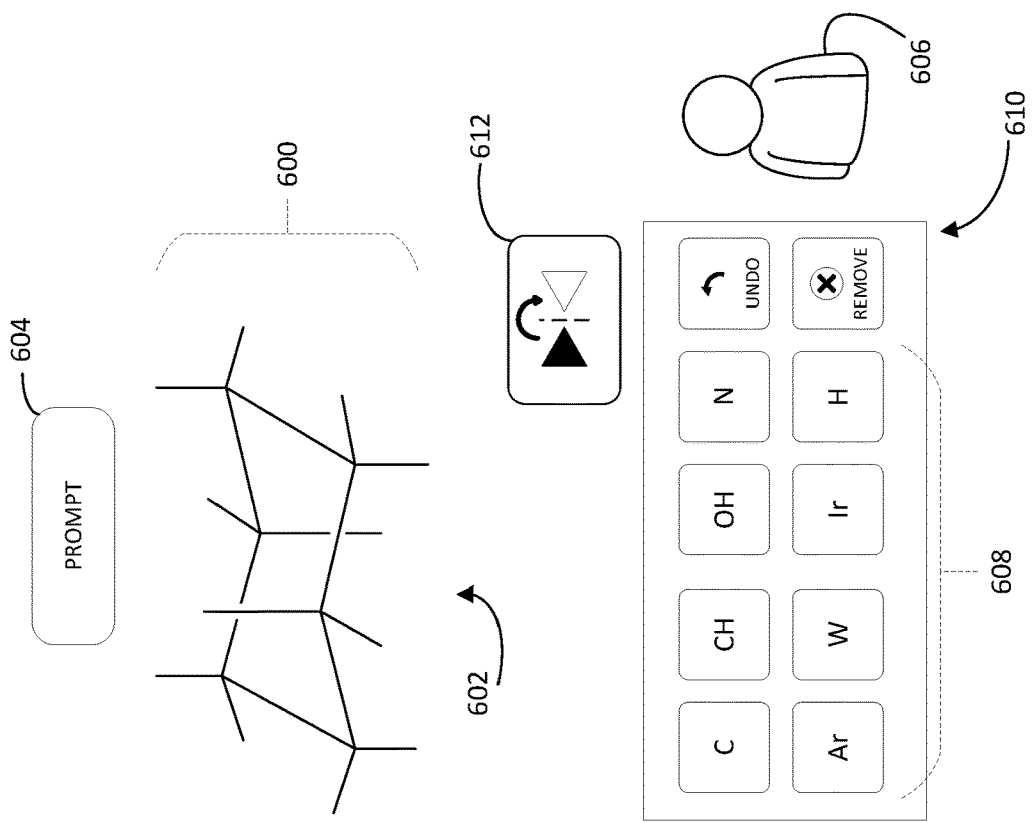
FIGS. 6A-6B illustrate the adaptive nature of an additional exemplary adaptive grid of a chemistry education application and/or system.
Figure 6B:
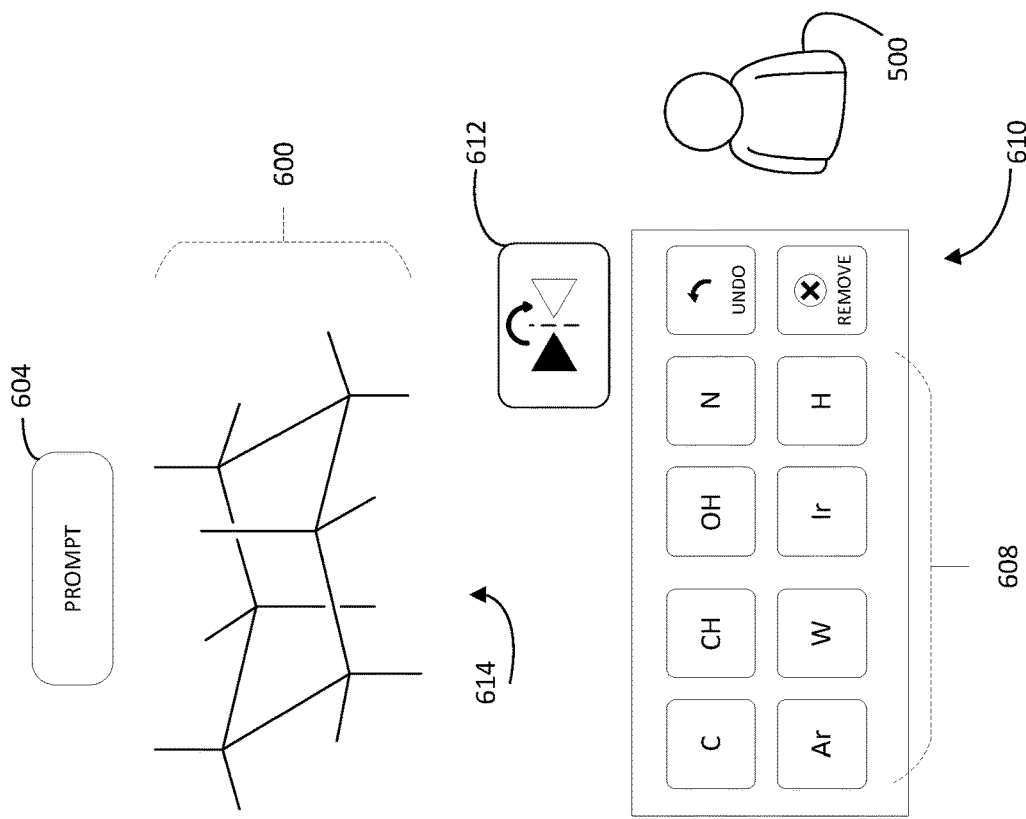

While FIGS. 2A-5D illustrate the adaptive nature of the hexagon grid and the extension grids, FIGS. 6A-6B illustrate an adaptive nature of another type of exemplary adaptive grid 600. The adaptive grid 600 illustrated in FIG. 6A is an adaptive molecular chair projection grid 602 on which a chair projection or conformer can be created. The adaptive chair projection grid 602 may, for example, replace the adaptive hexagon grid 212 of FIG. 2A, when the prompt 216 changes and directs the user to create a chemical structure that employs a chair conformer or projection.

Referring back to FIG. 6A, a prompt 604 directs a user 606 to create a chemical structure (e.g., a type of chair projection or conformer) on the adaptive chair projection grid 602. The user 606 can select an input location (i.e., a line selection) on the chair grid 602 and then select one of a plurality of exemplary inputs 608 from a smart suggestion keyboard 610 in substantially the same manner described above with respect to FIGS. 1A-5D. An exemplary flip function 612 of FIG. 6A can be employed by the user 606 to present a mirror image of the adaptive chair projection grid 602. For example, with reference to both FIGS. 6A and 6B, the user 606 selected the flip function 612 to cause the adaptive chair projection grid 602 (FIG. 6A) to be replaced with a mirrored imaged chair projection grid 614 as illustrated in FIG. 6B, thus illustrating the adaptive nature of the grid (compare the grid 602 of FIG. 6A with the grid 614 of FIG. 6B). The flip function 612 may also be employed to change the mirror imaged chair projection grid 614 of FIG. 6B back to the chair projection grid 602 of FIG. 6A. Further, the flip function 612 may also be employed when the adaptive chair grid (e.g., 602 or 614) includes inputs (e.g., one or more inputs 608 from the keyboard 610) thereon.

Figure 7A:
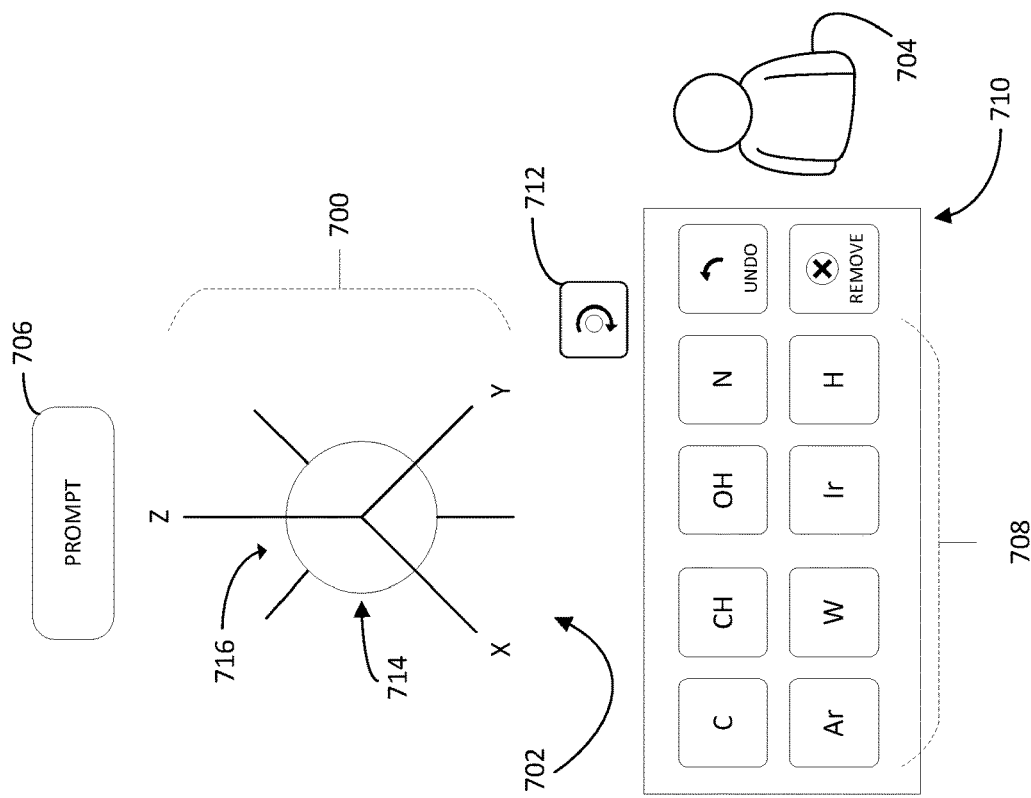
FIGS. 7A-7B illustrate the adaptive nature of another exemplary adaptive grid of a chemistry education application and/or system.
Figure 7B:
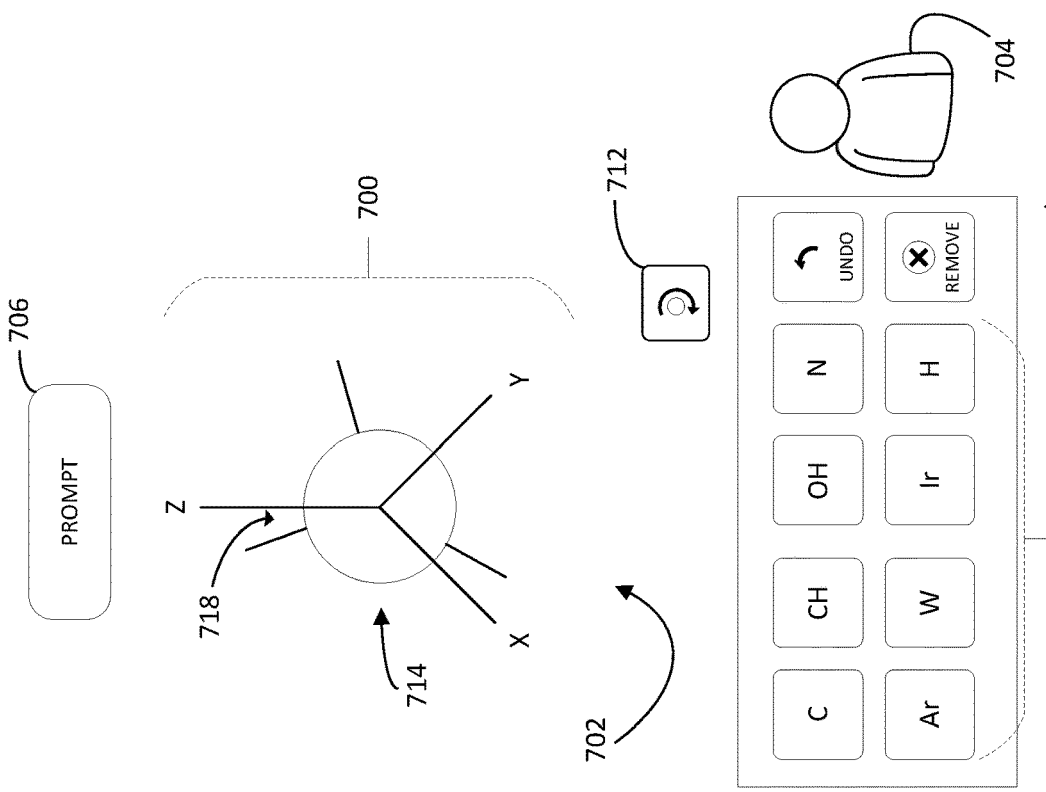

Referring now to FIGS. 7A-7B, yet another example of the adaptive nature of an exemplary adaptive molecule grid 700 is illustrated. The adaptive grid 700 of FIG. 7A is an adaptive Newman projection grid 702, where Newman conformers or projections can be created by a user 704 thereon. The adaptive Newman projection grid 702 may, for example, replace the adaptive hexagon grid 212 of FIG. 2A, when the prompt 216 changes and directs the user to create a chemical structure that employs a Newman conformer or projection.

With reference back to FIG. 7A, a prompt 706 directs the user 704 to create a chemical structure (e.g., a type of Newman projection or conformer) on the adaptive Newman projection grid 702. The user 704 can select input locations on the Newman projection grid 702 and then select exemplary inputs 708 from a smart suggestion keyboard 710 in substantially the same manner described above with respect to FIGS. 1A-5D to create a user created chemical structure to match the prompt 706. An exemplary rotation function 712 can be employed by the user 704 to rotate a portion 714 (often referred to as the distal carbon) of the grid 702. For example, with reference to FIGS. 7A and 7B, the user 704 selected the rotation function 712 to cause the portion 714 of the Newman projection grid 702 to rotate from a first position 716 (FIG. 7A) to a second position 718 (FIG. 7B), thus illustrating the adaptive nature of the adaptive Newman projection grid 702. The second position 718 may be referred to as an eclipsed conformation Newman projection grid.

The rotation function 712 may be employed even when the adaptive Newman grid 702 includes inputs (e.g., one or more inputs 708 from the keyboard 710) thereon. Further, the rotation function 712 may be employed to continue rotation of the portion 714 of the Newman projection grid 702 in a step-wise or fluid manner until it comes back to the first position 716 of FIG. 7A or to some other position.

Figure 8A:
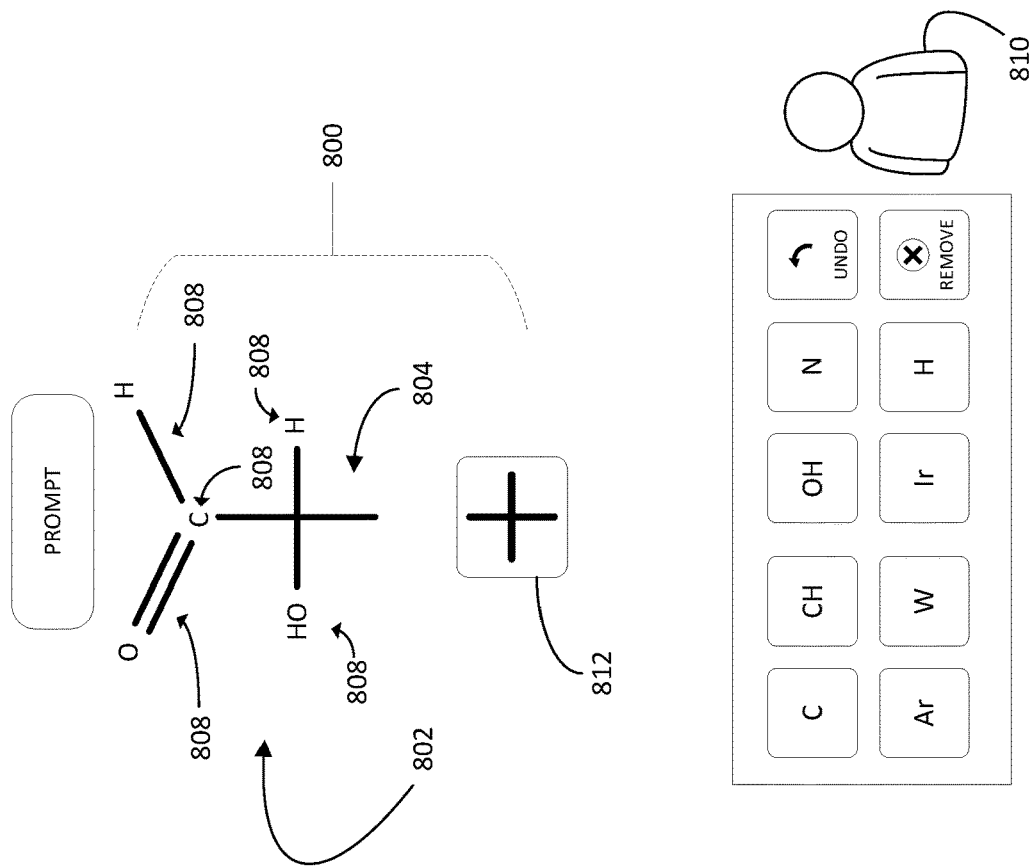
FIGS. 8A-8B illustrate the adaptive nature of yet another exemplary adaptive grid of a chemistry education application and/or system.
Figure 8B:
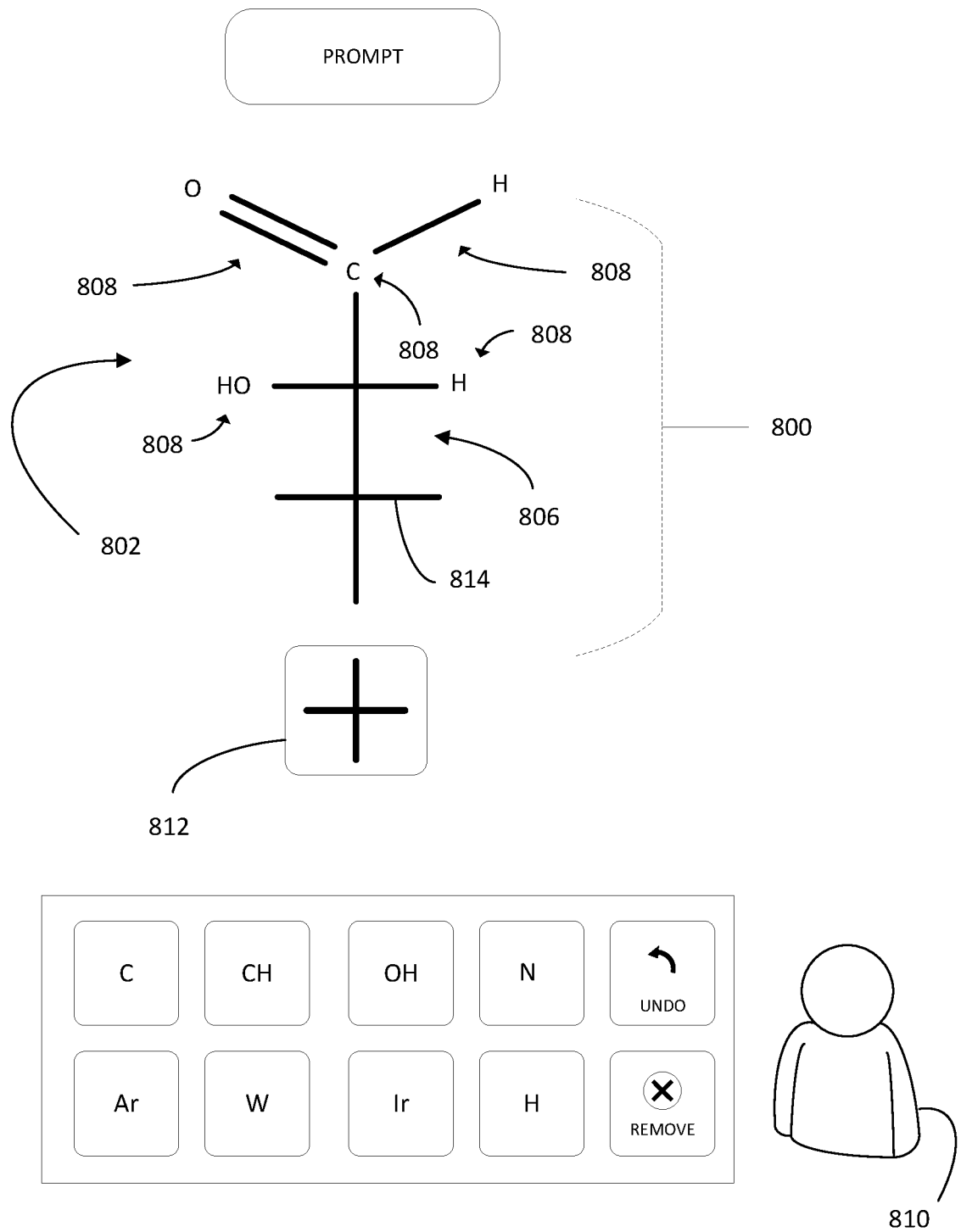

In yet another example, the adaptive nature of an exemplary adaptive molecule grid 800 is illustrated in FIGS. 8A-8B. The adaptive grid 800 of FIGS. 8A-8B is an exemplary adaptive Fischer projection grid 802. The adaptive Fischer projection grid 802 may, for example, replace the adaptive hexagon grid 212 of FIG. 2A when the prompt 216 changes and directs the user to create a chemical structure that employs a chair conformer or projection.

FIG. 8A represents the adaptive Fischer projection grid 802 in a first form 804 and FIG. 8B represents the adaptive Fischer projection grid 802 in a second form 806. Each form 804, 806 of the Fischer projection grid already includes a variety of exemplary inputs 808 thereon. One or more of the inputs 808 may have been selected by a user 810. Additionally, or alternatively, one or more of the exemplary inputs 808 may have been provided by the chemistry education application without user intervention. Further, as mentioned, these inputs 808 are merely exemplary and other examples may include different inputs or different inputs at different locations on the Fischer projection grid 802.

With continued reference to FIG. 8A, while the Fischer projection grid 802 is in the first form 804, the user 810 is given an option to add additional rungs to the Fischer projection grid 802 via an exemplary addition function 812. For example, the user 810 may select the addition function 812 to cause the Fischer projection grid 802 to adapt from the first form 804 of FIG. 8A to the second form 806 of FIG. 8B. As seen in the second form 806, an additional "rung" 814 (a.k.a., a grid line) has been appended to the grid 802 (compare the first form 804 of FIG. 8A with the second form 806 of FIG. 8B), thus illustrating the adaptive nature of the Fischer projection grid 802. While inputs 808 are illustrated on the Fischer projection grid 802, the addition function 812 may be employed on a Fischer projection grid without inputs already thereon. Further, in some example, an "undo" function from the keyboard may be employed to remove the rung.

Figure 9B:
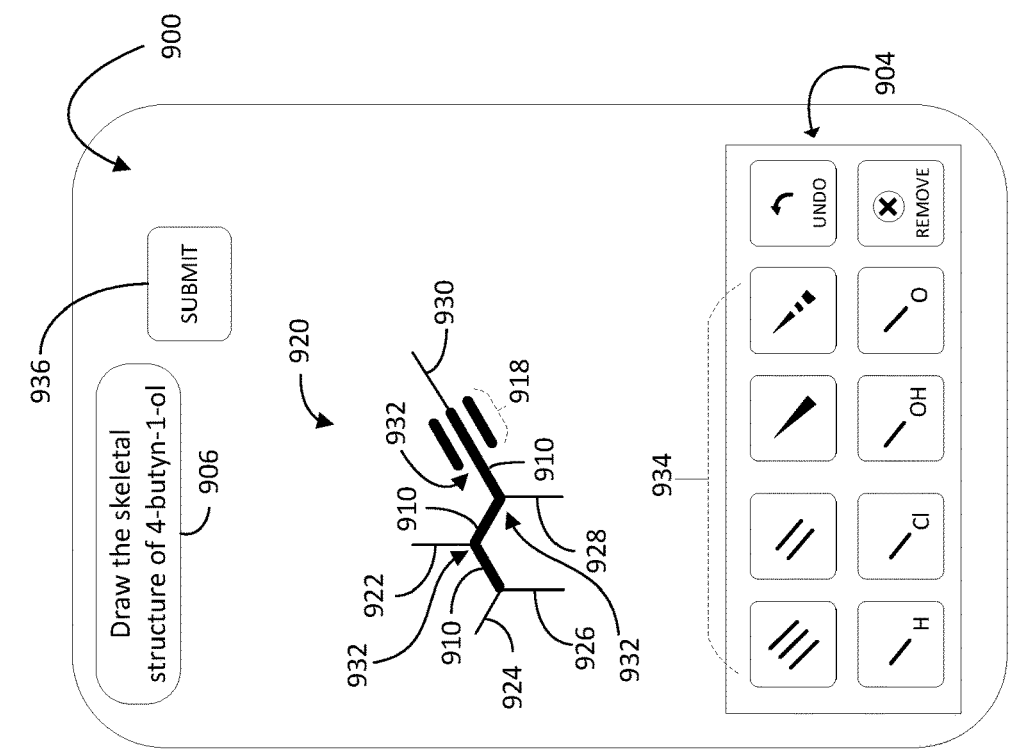
FIGS. 9A-9B illustrate the adaptive nature of yet another exemplary adaptive grid of a chemistry education application and/or system.
Figure 9A:
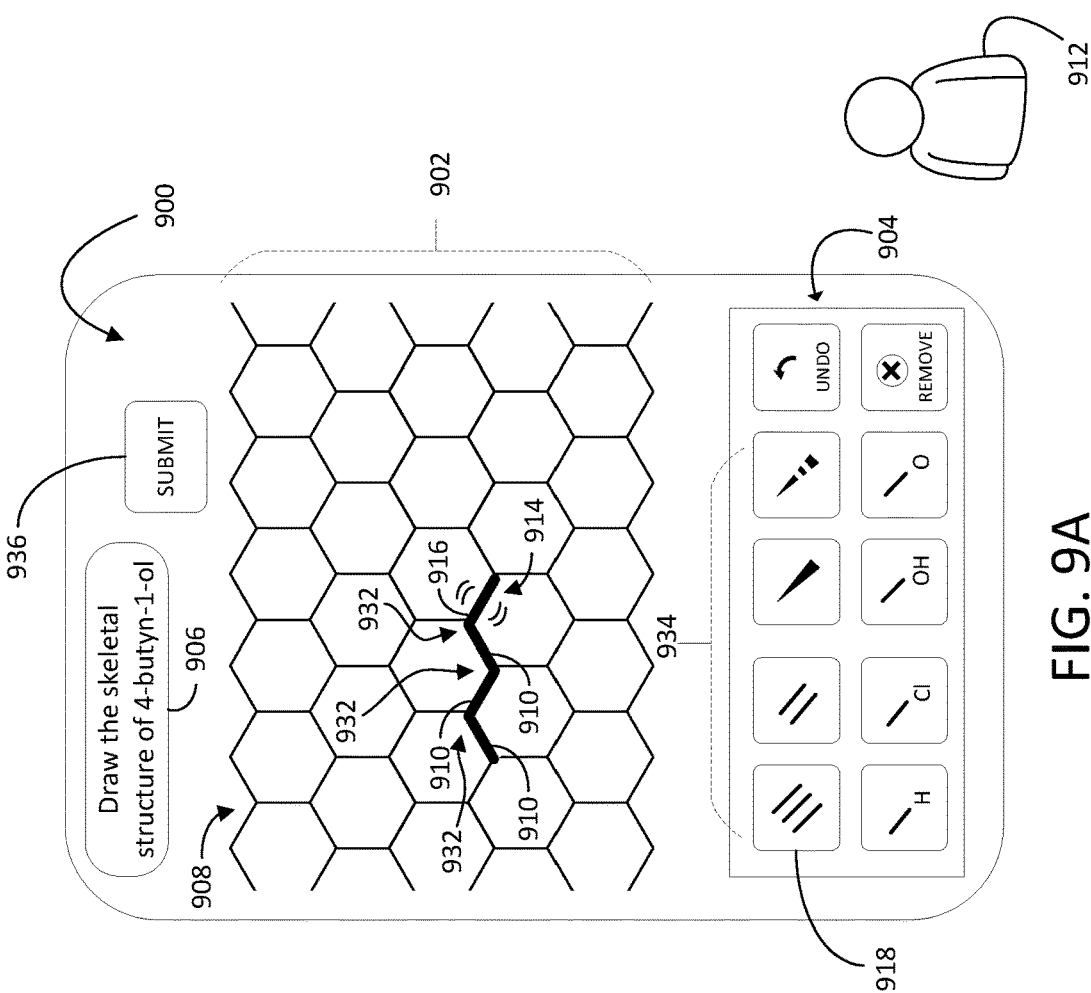

With reference now to FIGS. 9A-9B, an exemplary chemistry education application 900 illustrating additional exemplary adaptive features of adaptive grids is shown. An exemplary adaptive grid 902 is illustrated in FIG. 9A, along with an exemplary keyboard 904 and an exemplary prompt 906. The exemplary adaptive grid 902 is presented as an adaptive hexagon grid 908 having a plurality of exemplary bond representations 910 presented thereon. The bond representations 910 may have been previously selected by a user 912, or they may have been preloaded by the chemistry education application 900.

Before proceeding, it is noted that unlike some of the examples presented above, FIG. 9A illustrates an exemplary feature where default bond representations are employed. That is, and as will be described below, when a user selects a location, a default bond is presented thereon. The user is then allowed to change that default bond (i.e., make a keyboard selection) before making another grid location selection. Alternatively, the user may choose to keep the default bond and make another location selection from the grid. While this default bond feature is represented in FIGS. 9A-9B, as will be described below, such a feature may also be employed in the scenarios discussed above with respect to FIGS. 1A-8B. Similarly, instead of employing the default bond representation in the examples describe below with respect to FIGS. 9A-9B, the manner set forth above with respect to FIGS. 1A-8B, which does not employ default bond representations, could instead be employed.

With reference back to FIG. 9A, the user 912 has selected a grid location 914 and the chemistry education application 900 presented a default single covalent bond 916 thereon. That is, the user 912 did not select the single covalent bond 916 for the selected location 914, but rather, the chemistry education application 900 placed the default single covalent carbon bond 916 when the user 912 made the location selection 914. As discussed above, other examples may not employ the use of default bonds, but rather, leave the location selection 914 empty until the user 912 makes a selection from the keyboard 904.

Nonetheless, the example illustrated in FIG. 9A employs the default bond feature, and the default single covalent carbon bond 916 is flashing to indicate to the user 912 that a location selection has been made. Other indicators, however, may be employed. For example, the default bond 916, which also represents the selected grid location 914, may be presented in a color (e.g., red) different than the pre-existing bond representations 910. Regardless of the type of indicator employed, the indicator visually notifies the user 912 that the grid location 914 has been selected.

FIG. 9B illustrates that the user 912 chose not to retain the default bond 916, but rather, the user 912 selected a triple covalent bond 918 (see FIG. 9A) from the keyboard 904 to replace the default bond 916. Accordingly, the adaptive hexagon grid 908 of FIG. 9A has changed into a grid 920 (FIG. 9B) that includes grid lines 922, 924, 926, 928, 930 extending from molecule vertices 932 represented in FIG. 9A. Each of these grid lines 922-930 of FIG. 9B may later be individually selected by the user 912 in a manner previously described. It is noted that the triple covalent bond 918 is presented parallel to, and extending therefrom, the bond 910 it is conjoined with, as is convention. Further, the grid line 930 extending from the triple covalent bond 918 is parallel to the triple covalent bond 918.

While FIG. 9B illustrates five (5) extension or grid lines 922-930, in other examples fewer or greater extension lines may be employed.

Further, while FIGS. 9A and 9B illustrate keyboards 904 having the same inputs 934, other examples may employ keyboards with different inputs than those shown.

Figure 9C:
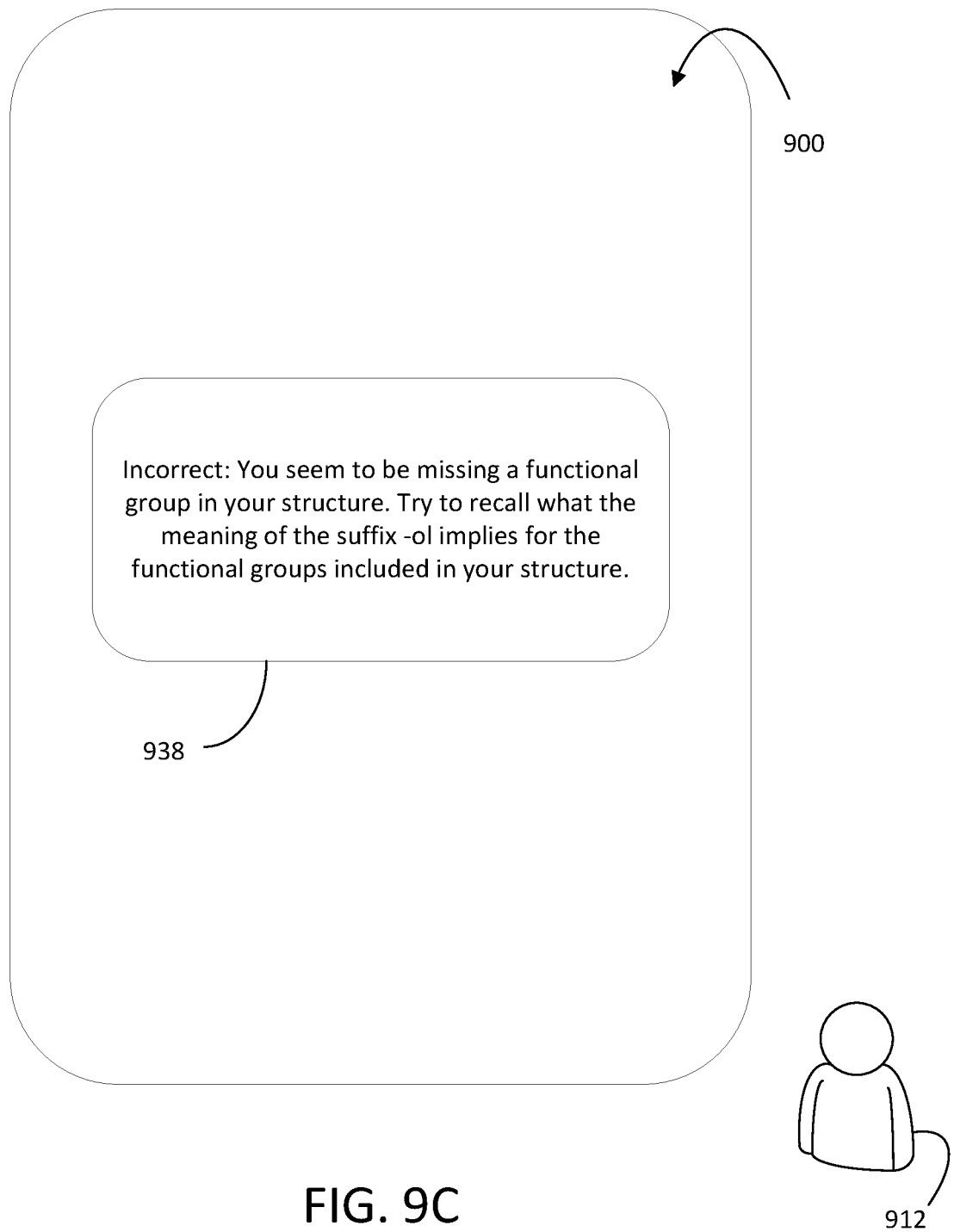
FIG. 9C illustrates an exemplary notification that may be employed by a chemistry education application.

Referring now to FIG. 9C, a scenario where the user 912 selected an exemplary submit feature 936 (FIG. 9B) after the structure of FIG. 9B was created is illustrated. As discussed in previously described figures, the submit feature 936 may be employed to determine if the user created structure is accurate. That is, the chemistry education application or system 900 determines if the user created structure (e.g., the molecular structure of FIG. 9B) is equivalent to the structure set forth in the prompt (e.g., the prompt 906 of FIG. 9B). Since the exemplary prompt 906 directs the user 912 to "Draw the skeletal structure of 4-butyn-1-ol," the structure represented in FIG. 9B is incorrect. Accordingly, after the user 912 selects submit 936 in this exemplary scenario, the chemistry education application 900 presents a notification 938 (see FIG. 9C) to the user 912. In this scenario, the exemplary notification 938 indicates to the user 912 that the structure of FIG. 9B is incorrect. If it were correct, the notification may indicate to the user 912 that the user created structure is correct.

In the exemplary scenario of FIG. 9B, however, the user created structure is not the structural representation for 4-butyn-1-ol. While not shown, a correct structure would include an HO functional group represented on the grid 900. Accordingly, the notification 938 of FIG. 9C may, for example, state the following: "Incorrect: You seem to be missing a functional group in your structure. Try to recall what the meaning of the suffix -ol implies for the functional groups included in your structure." That is, the notification 938 may provide a hint to the user 912 so that the user may attempt to correct the structure. As such, rather than stating which portion 910, 918 of the user created structure of FIG. 9B in incorrect, the notification 938 may instead provide a hint to guide the user 912 to the correct answer. This is in contrast to merely stating what portions of the structure is incorrect and telling the user what the correct structure looks like.

The hint provided in the notification of FIG. 9C is merely exemplary and other "hints" may instead be employed. Further, or alternatively, the notification 938 may merely indicate to the user whether the user created structure is correct or not, without showing a hint.

In scenarios where a hint is employed, the user 912 may then use the "hint" to correct (or attempt to correct) the chemical structure (i.e., to correct the molecular structure of FIG. 9B). Previously described functionality (e.g., remove function, undo function, and/or etc.) may then be employed by the user 912 to correct the structure.

By implementing hints, the chemistry education application engages the user 912 in experiential learning where the user is allowed to make mistakes and then attempt to correct those mistakes. This type of learning can often lead to long-term retention benefits for the user.

While FIG. 9C illustrates the notification 938 without any background or other features of the chemistry education application 900, in other examples the notification 938 may be displayed over graphical features of the chemistry education application 900.

Figure 10:
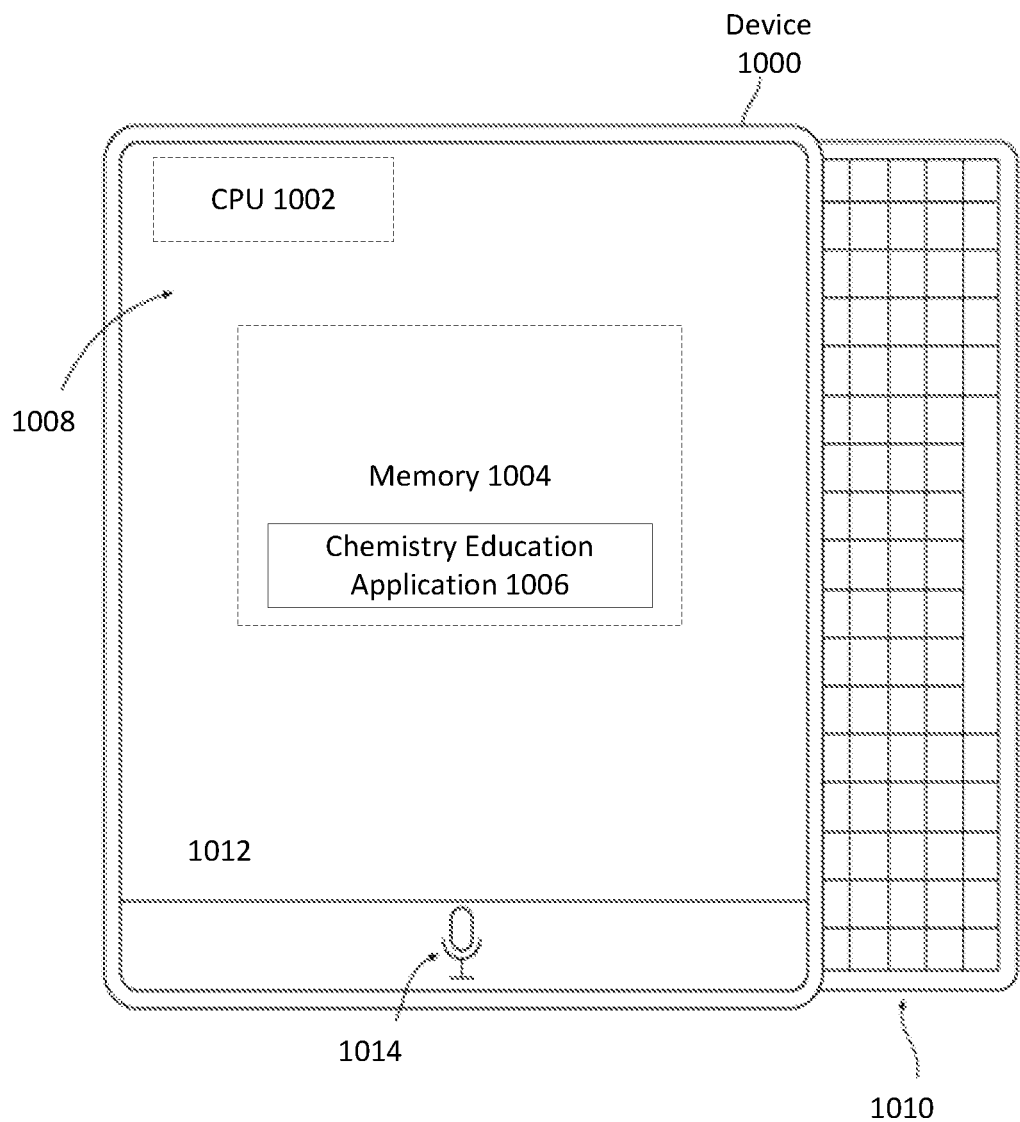
FIG. 10 illustrates an exemplary computing device or system having an exemplary chemistry education application operating thereon.

Referring now to FIG. 10, an exemplary computing device or system 1000 is shown having capabilities described herein. Computing devices such as the devices discussed herein may include a central processing unit (CPU) 1002 or processor, a memory 1004 having a Chemistry Education Application 1006 (e.g., the chemistry education application 200 along with its adaptive grids) stored thereon, a display 1008 (e.g., display 102), and an input mechanism. In conjunction with the memory 1004, the processor 1002 can carry out the actions of the chemistry education application 1006 (see FIGS. 1A-8B). For example, in conjunction with the chemistry education application 1006, the processor(s) 1002 is capable of creating a plurality of adaptive grids (e.g., adaptive grids 110, 212, 300, 400, 500, 600, 700, 800, respectively of FIGS. 1A-8A).

The input mechanism may, for example, include a keyboard 1010, a touchscreen 1012 and/or a microphone 1014. Other examples, not shown, are also contemplated, such as a mouse or stylus. The one or more input mechanisms (e.g., 1010-1014) may be employed for general control of the chemistry education application 910. For example, the touchscreen 1012 may be employed to make grid location selections (see e.g., location inputs 240, 242, 264, 268, 272, 276 of FIG. 2C) and/or bond selections from the smart suggestion keyboard selections (see e.g., visual keyboards 106, 214, 316, 508, 610, 710).

Figure 11:
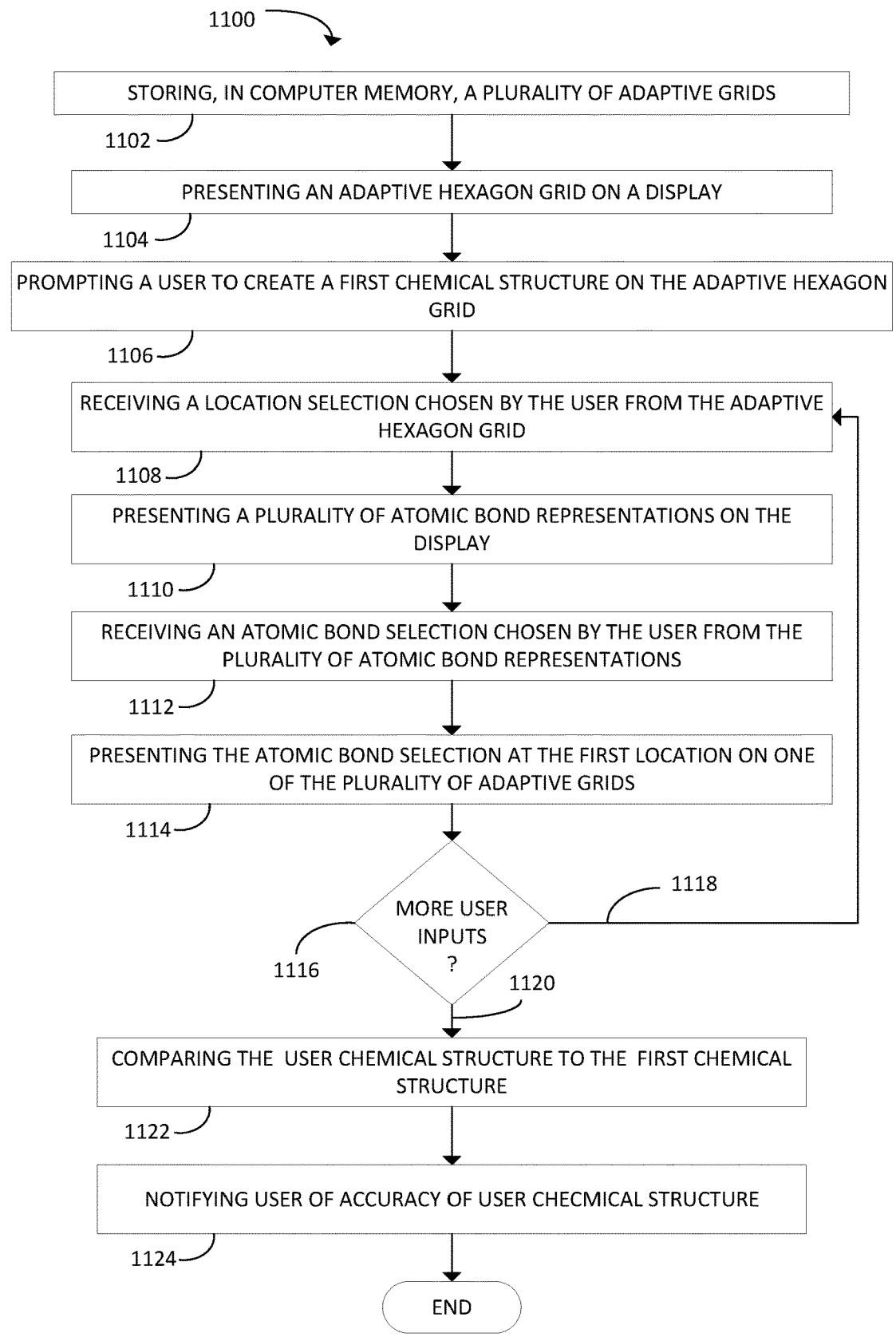
FIG. 11 illustrates an exemplary technique to provide chemistry education to a user.

With reference now to FIG. 11, a flowchart illustrates an exemplary technique 1100 to provide chemistry education to a user. Process control, which may be carried out by a computer processor(s), begins at block 1102, where an application such as an organic chemistry application stores a plurality of adaptive grids in computer memory. Process control then proceeds to block 1104, where presenting an adaptive hexagon grid on a display occurs. The adaptive hexagon grid is one of the plurality of adaptive grids. Further, the adaptive hexagon grid includes a plurality of conjoined hexagons that may be free of atomic bond lines.

Process control proceeds to block 1106 for prompting a user to create a first chemical structure on the adaptive hexagon grid. Once the user is prompted, process control proceeds to block 1108, where receiving a location selection chosen by the user occurs. The first location selection represents a first location on the adaptive hexagon grid. The user may make a selection (e.g., a first location selection) from the grid in a variety of ways. For example, the user may touch or tap a display on which the adaptive grid appears. Alternatively, the user may use a pointing device such as a mouse or stylus to make the selection. Other selection techniques may also be employed.

Once the location selection is made, process control proceeds to block 1110, where presenting a plurality of atomic bond representations on the display occurs. The plurality of atomic bond representations includes at least a single covalent bond representation and a double covalent bond representation. It is noted that in other exemplary techniques, presentation of first plurality of atomic bond representations may occur prior to the user making the location selection at block 1108.

In such techniques, however, where presenting of the plurality of atomic bond representations occurs after receiving the location selection at block 1108, each of the plurality of atomic bond representations may be oriented such that each, or some, is substantially parallel to the location selection.

With continued reference to the technique 1100 of FIG. 11, after the plurality of atomic bond representations are presented, process control continues to block 1112, where receiving an atomic bond selection chosen by the user occurs. The atomic bond selection (e.g., a first atomic bond selection) is chosen from the plurality of atomic bond representations.

Once the atomic bond selection is received from the user, process control proceeds to block 1114 for presenting the atomic bond selection at the selected location on one of the plurality of adaptive grids. As such, the atomic bond selection may be presented on the adaptive hexagon grid or another of the plurality of adaptive grids, where each grid shares the location. The user is effectively creating a proposed chemical structure, which the user hopes will be the same as the first chemical structure set forth in the prompt (1106).

Process control may then proceed to decision block 1116, where it is determined whether or not the user has completed the user's proposed chemical structure. This determination may, for example, be based on whether the user has indicated (e.g., selected submit 290 of FIG. 2C) that they have finished the proposed chemical structure.

If the user has not finished 1118 the attempt to make the first chemical structure, process control proceeds back to block 1108, where receiving an additional location selection by the user from the grid occurs. In such an instance, process control would continue as discussed above.

If, on the other hand, the user has finished 1120 the attempt to make the first chemical structure, process control proceeds block 1122, where comparing the user created chemical structure to the first chemical structure (i.e., the chemical structure provided in the prompt) occurs.

Such a comparison may be made by, for example, accessing a database that includes the first chemical structure and then comparing the proposed chemical structure (i.e., the user created chemical structure) to the first chemical structure.

After the comparison is made, process control proceeds to block 1124, where notifying the user of the accuracy of the user created chemical structure occurs. The user may, for example, be notified that the structure is accurate or is not accurate. Further, if the user created chemical structure is not accurate, process control may merely notify the user of the inaccuracy without notifying the user what component(s) of the structure is inaccurate. After the user is notified, process control proceeds to an end. In other exemplary techniques, however, the user may be given one or more opportunities to correct the user created chemical structure.

In other examples not shown in FIG. 11, process control may carry out additional operations. For example, process control may provide for orienting each of the first plurality of atomic bond representations on the display such that each atomic bond representation of the first plurality of atomic bond representations is substantially parallel to the first location of the adaptive hexagon grid after the first location selection is selected by the user. The first plurality of atomic bond representations may be free of ring extension representations.

Process control may continue with replacing the first plurality of atomic bond representations on the display with a second plurality of atomic bond representations after the user selects a second or additional location on the adaptive hexagon grid that is non-parallel to the first location. The second plurality of atomic bond representations may be oriented such that each atomic bond representation of the second plurality of atom bond representations is substantially parallel to the second location.

Still continuing, process control may provide for presenting a first appended grid line on the adaptive hexagonal grid after the user has caused a set of three atomic bond representations to appear on the adaptive hexagonal grid such that the set of three atomic bond representations meet at a first node. The first node is where two or more lines of the adaptive hexagon grid meet. Further, the first appended grid line may appear within an interior of a second hexagon of the adaptive hexagon grid and has a first end at the first node.

In addition to appending one or more lines, process control may also provide for removing a grid line that conjoins two faces of two hexagons of the adaptive hexagon grid when the user causes, for example, a double covalent bond oxygen (O) bond representation, a single covalent bond chlorine (Cl) bond representation, or a single covalent bond hydrogen (H) bond representation to appear on the adaptive hexagon grid.

With reference now back to FIGS. 1-11 discussed above, exemplary system(s) and devices may be any computing system and/or device that includes a processor (e.g., CPU 1002 of FIG. 10) and a memory (e.g., memory 1004). Computing systems and/or devices generally include computer-executable instructions (e.g., chemistry education application 200 of FIGS. 2A-2C and 1006 of FIG. 10), where the instructions may be executable by one or more computing devices such as those listed above and below. Computer-executable instructions may be compiled or interpreted from computer programs created using a variety of programming languages and/or technologies, including, without limitation, and either alone or in combination, Java™, C, C++, Visual Basic, Java Script, Perl, etc. The exemplary system(s), device(s), and items therein may take many different forms and include multiple and/or alternate components. While exemplary systems, devices, and modules are shown in the Figures, the exemplary components illustrated in the Figures are not intended to be limiting. Indeed, additional or alternative components and/or implementations may be used, and thus the above examples should not be construed as limiting.

In general, computing systems and/or devices may employ any of a number of computer operating systems, including, but by no means limited to, versions and/or varieties of the Microsoft Windows® operating system, the Unix operating system (e.g., the Solaris® operating system distributed by Oracle Corporation of Redwood Shores, California), the AIX UNIX operating system distributed by International Business Machines of Armonk, New York, the Linux operating system, the Mac OS X and iOS operating systems distributed by Apple Inc. of Cupertino, California, the BlackBerry OS distributed by Research In Motion of Waterloo, Canada, and the Android operating system developed by the Open Handset Alliance. Examples of computing systems and/or devices include, without limitation, personal computers, cell phones, smart-phones, super-phones, tablet computers, next generation portable devices, handheld computers, secure voice communication equipment, or some other computing system and/or device.

Further, the processor or the microprocessor (e.g., CPUs 1002) of computing systems and/or devices receives instructions from the memory (e.g., memory 1004) and executes these instructions, thereby performing one or more processes, including one or more of the processes described herein. Such instructions and other data may be stored and transmitted using a variety of computer-readable mediums (e.g., memory 1004).

A CPU or processor may include processes comprised from any hardware, software, or combination of hardware or software that carries out instructions of a computer programs by performing logical and arithmetical calculations, such as adding or subtracting two or more numbers, comparing numbers, or jumping to a different part of the instructions. For example, the CPU 1002 of FIG. 10 may be any one of, but not limited to single, dual, triple, or quad core processors (on one single chip), graphics processing units, visual processing units, and virtual processors.

Memory (e.g., 1004) may be, in general, any computer-readable medium (also referred to as a processor-readable medium) that may include any non-transitory (e.g., tangible) medium that participates in providing data (e.g., instructions) that may be read by a computer (e.g., by CPUs 1002 of exemplary mobile device 1000). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including radio waves, metal wire, fiber optics, and the like, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

With further regard to FIGS. 1-11 and the processes, systems, methods, techniques, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description or Abstract below, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary. Further, the use of terms such as "first," "second," "third," and the like that immediately precede an element(s) do not necessarily indicate sequence unless set forth otherwise, either explicitly or inferred through context.

The invention claimed is:

1. A non-transitory computer-readable medium storing instructions executable by one or more hardware processor(s) to:
   store a plurality of adaptive grids on a computer memory;
   display an adaptative hexagon grid in a drawing window on a computing device display, wherein the adaptive hexagon grid is one of the plurality of adaptive grids, and wherein the adaptive hexagon grid comprises lines forming a plurality of conjoined hexagons;
   store a first chemical structure on the computer memory;
   prompt a user, via the computing device display, to create the first chemical structure on the adaptive hexagon grid displayed on the computing device display;
   receive a first location selection, via a user-controlled input mechanism, of a location of a line on the adaptive hexagon grid;
   store the first location selection on the computer memory;
   display a first plurality of icons on the computing device display, wherein the first plurality of icons comprise atomic bond representations for at least a single covalent bond and a double covalent bond;
   receive a first atomic bond selection from the first plurality of atomic bond icons via the user-controlled input mechanism;
   store the first atomic bond selection on the computer memory; and
   display the first atomic bond selection at the location of the line on the adaptive hexagon grid displayed the computing device display.

2. The non-transitory computer-readable medium of claim 1 storing further instructions executable by the hardware processor to:
   orient the first plurality of atomic bond representations on the computing device display such that each atomic bond representation of the first plurality of atomic bond representations is substantially parallel to the first location selection on the adaptive hexagon, wherein the first plurality of atomic bond representations is free of ring extension representations;
   receive a second location selection, via the user-controlled input mechanism from the adaptive hexagon grid, wherein the second location selection is non-parallel to the first location selection; and
   replace the first plurality of atomic bond representations on the computing device display with a second plurality of atomic bond representations after reception of the second location selection, wherein the second plurality of atomic bond representations is oriented such that each atomic bond representation of the second plurality of atom bond representations is substantially parallel to the second location selection, and wherein the non-transitory computer readable storage medium comprises the computer memory.

3. The non-transitory computer-readable medium of claim 1 wherein the one of the plurality of adaptive grids is the adaptive hexagon grid such that the first atomic bond selection displayed at the first location selection is displayed at the first location on the adaptive hexagon grid, and wherein at least one hexagon of the plurality of hexagons is surrounded by six other hexagons.

4. The non-transitory computer-readable medium of claim 3 storing further instructions executable by the hardware processor to display a first appended grid line on the adaptive hexagonal grid after the user has caused a set of three atomic bond representations to appear on the adaptive hexagonal grid such that the set of three atomic bond representations meet at a first node, wherein the first node is where three lines of the adaptive hexagon grid meet, and wherein the first appended grid line appears within an interior of a second hexagon of the adaptive hexagon grid and has a first end at the first node.

5. The non-transitory computer-readable medium of claim 3 storing further instructions executable by the hardware processor to:
   receive, via the user-controlled input mechanism, an input to display at least one of a double covalent bond oxygen (O) bond representation, a single covalent bond chlorine (Cl) bond representation, a single covalent bond hydrogen (H) bond representation on the adaptive hexagon grid; and
   after the reception of the input, remove a grid line that conjoins two faces of two hexagons of the adaptive hexagon grid.

6. The non-transitory computer-readable medium of claim 3 storing further instructions executable by the hardware processor to:
   display, on the computing device display, an adaptive chair projection grid comprising a skeleton of a molecular Chair conformer, wherein the adaptive chair projection grid is one of the plurality of adaptive grids and replaces the adaptive hexagon grid;
   prompt, via the computing device display, the user to create a second chemical structure on the adaptive chair grid;
   display a user-selected atomic symbol on the adaptive chair projection grid; and
   receive, via the user controlled input mechanism, a user input to replace the adaptive chair projection grid on the computing device display with a mirror image of the adaptive Chair projection grid.

7. The non-transitory computer-readable medium of claim 3 storing further instructions executable by the hardware processor to:
   replace the adaptive hexagon grid on the computing device display with one of: (i) an adaptive Fischer projection grid comprising a skeleton of a molecular Fischer conformer and (ii) an adaptive Newman projection grid comprising a skeleton of a molecular Newman conformer, wherein the adaptive Fischer projection grid and the adaptive Newman projection grid are each one of the plurality of adaptive grids;
   prompt the user to create a second chemical structure on one of the adaptive Fischer projection grid and the Newman projection grid; and
   receive a user input, via the user-controlled input mechanism, to one of: (i) append grid lines onto the adaptive Fischer projection grid and (ii) rotate portions of the adaptive Newman projection grid on the computing device display to create an eclipsed conformation Newman projection grid.

8. The non-transitory computer-readable medium of claim 3 wherein the one of the plurality of adaptive grids comprises one of a triangle extension grid having a three-carbon ring thereon, a square extension grid having a four-carbon ring thereon, and a pentagon extension grid having a five carbon ring thereon, and wherein the one of the plurality of adaptive grids further comprises at least one selectable grid line the user can add a chemical structure thereto.

9. A method carried out by at least one hardware processor, the method comprising:
 storing, in computer memory, a plurality of adaptive grids;
 displaying an adaptive hexagon grid on a computing device display, wherein the adaptive hexagon grid is one of the plurality of adaptive grids, and wherein the adaptive hexagon grid comprises lines forming a plurality of conjoined hexagons;
 storing a first chemical structure in the computer memory;
 prompting, via the computing device display, a user to create a first chemical structure on the adaptive hexagon grid displayed on the computing device display;
 receiving, via a user-controlled input mechanism, a first location selection, wherein the first location selection represents a first location of a line on the adaptive hexagon grid;
 storing the first location selection in the computer memory;
 displaying a first plurality of atomic bond representations on the computing device display as a first plurality of icons, wherein the first plurality of atomic bond representations comprises at least a single covalent bond representation and a double covalent bond representation;
 receiving, via the user-controlled input mechanism, a first atomic bond selection from the first plurality of icons, wherein the first atomic bond selection represents one atomic bond representation of the plurality of atomic bond representations;
 storing the first atomic bond selection in the computer memory; and
 displaying the first atomic bond selection at the first location on the computing device display, wherein the first location is retrieved from the computer memory.

10. The method of claim 9 further comprising:
 orienting each of the first plurality of atomic bond representations on the computing device display such that each atomic bond representation of the first plurality of atomic bond representations is substantially parallel to the first location of the adaptive hexagon grid after the first location selection, wherein the first plurality of atomic bond representations is free of ring extension representations; and
 replacing the first plurality of atomic bond representations on the computing device display with a second plurality of atomic bond representations after receiving input of a second location on the adaptive hexagon grid that is non-parallel to the first location, wherein the second plurality of atomic bond representations is oriented such that each atomic bond representation of the second plurality of atom bond representations is substantially parallel to the second location.

11. The method of claim 9 further comprising displaying a first appended grid line on the adaptive hexagonal grid on the computing device display after receiving input of three atomic bond representations to appear on the adaptive hexagonal grid such that the set of three atomic bond representations meet at a first node, wherein the first node is where three lines of the adaptive hexagon grid meet, and wherein the first appended grid line appears within an interior of a second hexagon of the adaptive hexagon grid and has a first end at the first node.

12. The method of claim 9 further comprising:
 receiving, via the user-controlled input mechanism, an input to display at least one of a double covalent bond oxygen (O) bond representation, a single covalent bond chlorine (Cl) bond representation, a single covalent bond hydrogen (H) bond representation on the adaptive hexagon grid; and
 removing, after receiving the input, a grid line that conjoins two faces of two hexagons of the adaptive hexagon grid.

13. The method of claim 9 wherein the one of the plurality of adaptive grids comprises one of a triangle extension grid having a three-carbon ring thereon, a square extension grid having a four-carbon ring thereon, and a pentagon extension grid having a five carbon ring thereon, and wherein the one of the plurality of adaptive grids further comprises at least one selectable grid line the user can add a chemical structure thereto.

14. The method of claim 9 further comprising:
 replacing the adaptive hexagon grid on the computing device display with one of: (i) an adaptive Fischer projection grid comprising a skeleton of a molecular Fischer conformer, (ii) an adaptive Newman projection grid comprising a skeleton of a molecular Newman conformer, and (iii) an adaptive Chair projection grid comprising a skeleton of a molecular chair conformer, wherein the plurality of adaptive grids comprise the adaptive Fischer projection grid, the adaptive Newman projection grid, and the adaptive chair grid;
 prompting the user to create a second chemical structure on one of the adaptive Fischer projection grid, the Newman projection grid, and the adaptive chair projection grid; and
 receiving a user input to one of: (i) append grid lines onto the adaptive Fischer projection grid, (ii) rotate portions of the adaptive Newman projection grid to create an eclipsed conformation Newman projection grid, and (iii) replace the adaptive chair grid with a mirror image of the adaptive chair grid.

15. A system comprising:
 a plurality of adaptive grids, configured to be displayed on a computing device display;
 an adaptative hexagon grid, configured to be displayed on the computing device display, comprising lines forming a plurality of conjoined hexagons, wherein the adaptive hexagon grid is one of the plurality of adaptive grids, and wherein the adaptive hexagon grid is configured to receive, from a user-controlled input mechanism, a selection of a first location of a line on the adaptative hexagon grid; and
 a first plurality of atomic bond icons displayed on the computing device display, wherein the first plurality of atomic bond icons comprises a plurality of atomic bond representations comprising at least a single covalent bond representation and a double covalent bond representation,
 wherein the system is configured to display a first atomic bond representation at the first location on one of the plurality of adaptive grids displayed on the computing device display, and wherein the first atomic bond representation is one of the plurality of atomic bond representations selected via the user-controlled input mechanism.

16. The system of claim 15, the system further configured to:
 orient the first plurality of atomic bond representations on the computing device display such that each atomic bond representation of the first plurality of atomic bond representations is substantially parallel to the first location on the adaptive hexagon grid after receiving input of the first location, wherein the first plurality of atomic bond representations is free of ring extension representations; and replace the first plurality of atomic bond representations with a second plurality of atomic bond representations after receiving input of a second location on the adaptive hexagon grid that is non-parallel to the first location, wherein the second plurality of atomic bond representations is oriented such that each atomic bond representation of the second plurality of atom bond representations is substantially parallel to the second location.

17. The system of claim 15, the system further configured to append a grid line on the adaptive hexagonal grid after receiving input of a set of three atomic bond representations to appear on the adaptive hexagonal grid such that the set of three atomic bond representations meet at a first node, wherein the first node is where three lines of the adaptive hexagon grid meet, and wherein the first grid line appears within an interior of a second hexagon of the adaptive hexagon grid and has a first end at the first node.

18. The system of claim 15, the system further configured to:

receive, via the user-controlled input mechanism, an input to display at least one of a double covalent bond oxygen (O) bond representation, a single covalent bond chlorine (Cl) bond representation, a single covalent bond hydrogen (H) bond representation on the adaptive hexagon grid;

remove, after reception of the input, a grid line that conjoins two faces of two hexagons of the adaptive hexagon grid.

19. The system of claim 15, wherein the plurality of adaptive grids further include at least one of an adaptive chair projection grid, an adaptive Fischer projection grid, and a Newman projection, the system further configured to:

display one of the adaptive chair projection grid, the adaptive Fischer projection grid, and the Newman projection grid to replace the adaptive hexagon grid;

prompt the user to create a second chemical structure on one of the plurality of adaptive grids;

receive an append input to append grid lines onto the adaptive Fischer projection grid;

receive a rotate input to rotate portions of the adaptive Newman projection grid to create an eclipsed conformation Newman projection grid; and receive a rotate input to replace the adaptive chair projection grid on the computing device display with a mirror image of the adaptive Chair projection grid.

20. The system of claim 15 wherein (i) the one of the plurality of adaptive grids comprises one of a triangle extension ring, a square extension ring, and a pentagon extension ring, (ii) the one of the plurality of adaptive grids further comprises at least one selectable grid line the user can add a chemical structure thereto, and (iii) the first location on the one of the plurality of adaptive grids is at a same position as the first location on the adaptive hexagon grid.

* * * * *